(12) United States Patent
Tanio et al.

(10) Patent No.: US 7,549,981 B2
(45) Date of Patent: *Jun. 23, 2009

(54) SANITARY NAPKIN

(75) Inventors: Toshiyuki Tanio, Mitoyo-gun (JP);
Wataru Yoshimasa, Mitoyo-gun (JP)

(73) Assignee: Uni-Charm Corporation, Ehime (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/401,820

(22) Filed: Apr. 10, 2006

(65) Prior Publication Data
US 2006/0271008 A1 Nov. 30, 2006

(30) Foreign Application Priority Data
May 27, 2005 (JP) .............................. 2005-156100

(51) Int. Cl.
*A61F 13/15* (2006.01)
*A61F 13/20* (2006.01)

(52) U.S. Cl. ............................ 604/385.17; 604/385.01; 604/385.03

(58) Field of Classification Search ............ 604/385.01, 604/367, 385.101, 385.17
See application file for complete search history.

(56) References Cited

U.S. PATENT DOCUMENTS 4,046,147 A * 9/1977 Berg .................... 604/385.201
5,833,680 A * 11/1998 Hartman ................. 604/385.17
6,371,948 B1 * 4/2002 Mizutani ................ 604/385.01
6,676,649 B2 * 1/2004 Mizutani ..................... 604/387
2006/0142724 A1 * 6/2006 Watanabe et al. ....... 604/385.04

FOREIGN PATENT DOCUMENTS

| EP | 0 768 070 A1 | * | 4/1997 |
| JP | 11-033054 A | | 2/1999 |
| JP | 11-318979 A | | 11/1999 |
| JP | 2000-083993 A | | 3/2000 |
| JP | 2001-504727 A | | 4/2001 |
| JP | 2002-159534 A | | 6/2002 |
| WO | WO-98/22060 A1 | | 5/1998 |

* cited by examiner

*Primary Examiner*—Michele Kidwell
(74) *Attorney, Agent, or Firm*—Darby & Darby P.C.

(57) ABSTRACT

A sanitary napkin includes a main body having a liquid-absorbent layer for absorbing and retaining liquid and a projection disposed on a body surface of the main body. The projection has a resistive portion provided with a resistive member for resisting compressive deformation of the projection toward the main body and a flexible portion not provided with the resistive member. The flexible portion is longitudinally stretchable and subjected to a longitudinal elastic contractive force.

8 Claims, 19 Drawing Sheets

SANITARY NAPKIN

CROSS REFERENCE TO RELATED APPLICATION

This application claims the benefit of priority from Japanese Patent Application No. 2005-156100, filed on May 27, 2005, which is incorporated herein by reference in its entirety.

BACKGROUND OF THE INVENTION

1. Field of the Invention

The present invention relates to a sanitary napkin with a projection on a body surface of a main body, and more particularly to a sanitary napkin whose projection can easily conform to the contour of the wearer's crotch, ensuring contact with the wearer's body so as to be effective in preventing leakage of menstrual blood.

2. Description of the Related Art

There have been known sanitary napkins of the type including a main body with a liquid-absorbent layer and a projection disposed on the body surface of the main body.

Japanese Unexamined Patent Application Publication No. H11-33054 discloses a sanitary napkin including a liquid-absorbent layer and a topsheet covering the body surface of the liquid-absorbent layer. The body surface of the sanitary napkin is formed with a groove where the topsheet and the liquid-absorbent layer are pressed together. The groove defines a longitudinally elongated enclosure. The enclosure bulges beyond the surround surface.

Japanese Unexamined Patent Application Publication No. 2000-83993 discloses a sanitary napkin whose liquid-absorbent layer is composed of separate upper and lower cores. The lower core is integral with a liquid-impermeable lower sheet. On the body surface side of the lower core, there is provided a liquid-permeable upper sheet. Front and rear ends of the upper sheet are secured to the lower core, and elastic members are secured to the upper sheet in order to exert a longitudinal elastic contractive force. The upper core is also secured to the upper sheet. The upper core, as well as the upper sheet, can be raised from the lower core by the elastic contractive force. The upper core can face the wearer's vulva while the outer surface of the lower sheet is attached to the inner surface of a crotch portion of an undergarment. Since the upper core is movable independently of the lower core, the upper core can easily be kept in contact with the vulva to absorb menstrual blood, thereby preventing leakage of menstrual blood out of the napkin.

In the sanitary napkin disclose in JP H11-33054, as set forth above, the enclosure defined by the groove is relatively thick and elongated longitudinally of the sanitary napkin. Since the surface deformation properties and compression properties under body pressure are almost uniform within the enclosure, the enclosure cannot readily conform to the contour of the wearer's crotch, i.e., follow the irregularities due to the vaginal opening surrounded by the labia majora, the posterior commissure of labia majora, the perineum, the anus, and the intergluteal cleft. In addition, since the thickness of the enclosure is maintained only by the liquid-absorbent layer, when the liquid-absorbent layer is wetted and compressed by the body pressure, the enclosure will be inferior in compression recovery, creating a clearance between the wearer's crotch and the sanitary napkin.

In the sanitary napkin disclose in JP 2000-83993, on the other hand, the upper core can easily be kept in contact with the vaginal opening. In front of and behind the upper core, however, nothing is provided between the upper sheet and the lower core. Therefore, when the upper core is pushed down into contact with the lower core by the body pressure, it is difficult to keep the upper sheet in contact with the wearer's body in front of and behind the upper core. Particularly, it is difficult to keep the upper sheet in contact with the perineum and the anus.

If the sanitary napkin is not kept in contact with the perineum and the anus, for example, menstrual blood cannot be prevented from migrating rearwardly from the vaginal opening in a sleeping or chair-sitting position, thereby causing rearward leakage of menstrual blood.

SUMMARY OF THE INVENTION

The present invention has been developed to solve the problems in the prior art and has an object to provide a sanitary napkin with a projection which can easily conform to a shallow recess and a deep cleft of the wearer's body, improving contact with the wearer's crotch so as to be effective in preventing rearward leakage of menstrual blood.

According to the present invention, there is provided a sanitary napkin comprising:

a main body having a liquid-absorbent layer for absorbing and retaining liquid; and a projection disposed on a body surface of the main body, wherein the projection has a resistive portion provided with a resistive member for resisting compressive deformation of the projection toward the main body and a flexible portion not provided with the resistive member, the flexible portion being longitudinally stretchable and subjected to a longitudinal elastic contractive force.

In the sanitary napkin of the present invention, the resistive member makes the resistive portion of the projection more resistant to the compressive deformation than the flexible portion. When the resistive portion is brought into contact with the wearer's body, the flexible portion can be stretched under a body pressure to conform to the contour of the wearer's body, ensuring contact of the projection with the wearer's body.

In the present invention, preferably the main body is capable of being longitudinally curved by the longitudinal elastic contractive force acting on the flexible portion of the projection, wherein a bending stiffness in a direction of the curvature is higher in an area provided with the resistive member than in the other area. Since the bending stiffness of the napkin is locally increased by the resistive member, the napkin can easily be curved along the wearer's body with the resistive portion as the fulcrum.

Preferably, the resistive member is located behind a vagina-facing reference position, and the flexible portion has front and rear flexible portions in front of and behind the resistive member. This arrangement ensures that the resistive portion comes into contact with at least one of the posterior commissure of labia majora, the perineum, and the anus while the front and rear flexible portions come into contact with the vaginal opening and the intergluteal cleft, respectively, whereby the projection can follow the irregularities of the wearer's body.

According to one embodiment, the resistive member may be a stiffening member disposed on rising walls of the projection.

According to another embodiment, the resistive member may be a stiffening member disposed between the projection and the main body. In this case, a projection-forming member may be disposed on a body surface side of the main body along a longitudinal centerline of the main body to overlie the stiffening member.

According to still another embodiment, the resistive member may be a hump bulging from the body surface of the main body. In this case, the hump may be formed by locally increasing a basis weight of the liquid-absorbent layer. Preferably, the projection includes a cover sheet that covers the hump and is subjected to a longitudinal elastic contractive force, the cover sheet being secured to the hump but remaining unsecured to the main body in front of and behind the hump. This ensures contact of the cover sheet with the wearer's body due to flexible deformation at the portion remaining unsecured to the main body. The hump may include a plurality of longitudinally spaced humps.

In the sanitary napkin according to the present invention, as described above, the resistive portion of the projection can easily be kept in contact with the wearer's body, while the flexible portion of the projection can easily follow the irregularities of the wearer's body. This is effective in eliminating the clearance between the sanitary napkin and the wearer's body from the vaginal opening to the intergluteal cleft, preventing rearward leakage of menstrual blood, for example, in a sleeping or sitting position.

BRIEF DESCRIPTION OF THE DRAWINGS

The present invention will be understood more fully from the detailed description given hereinafter and from the accompanying drawings of the preferred embodiments of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
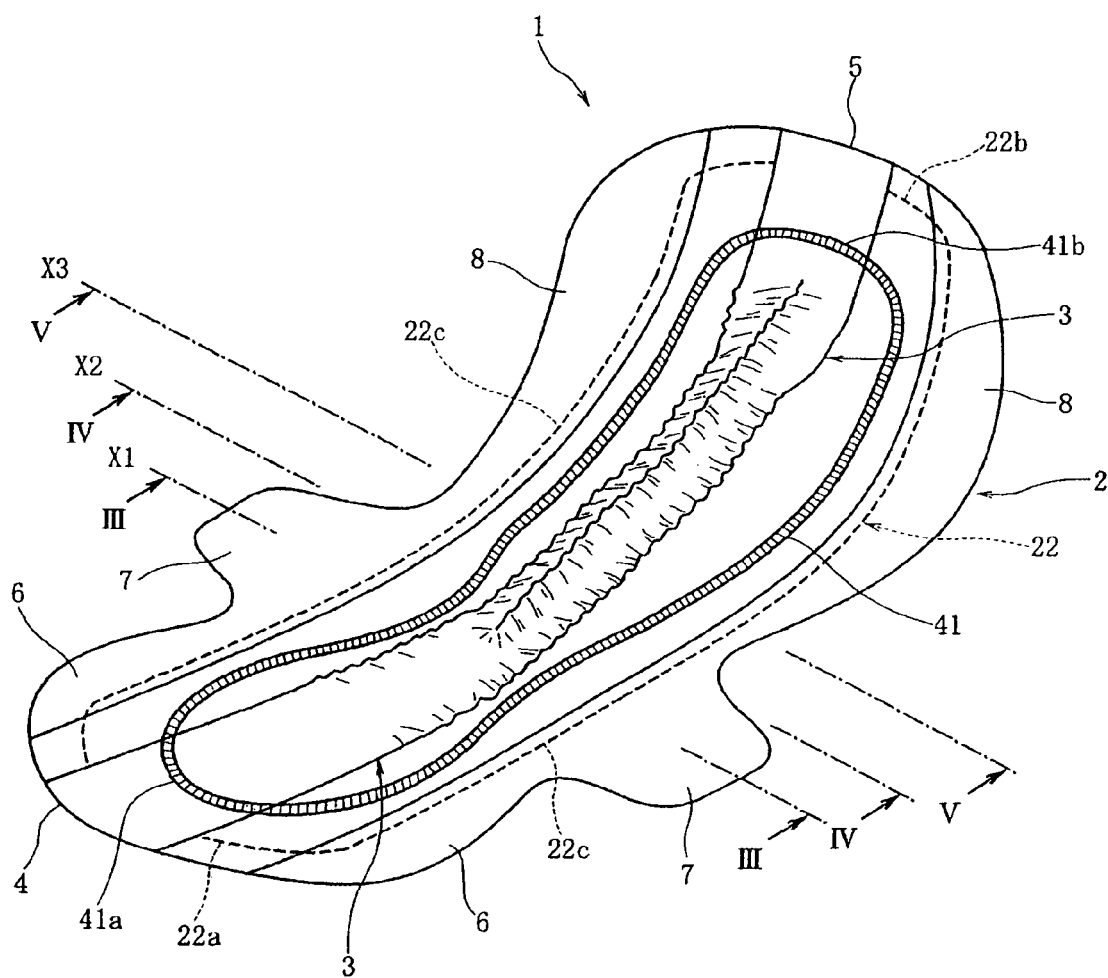
FIG. 1 is a perspective view of a sanitary napkin according to a first embodiment of the present invention in a state where no external force is exerted thereon.
Figure 2:
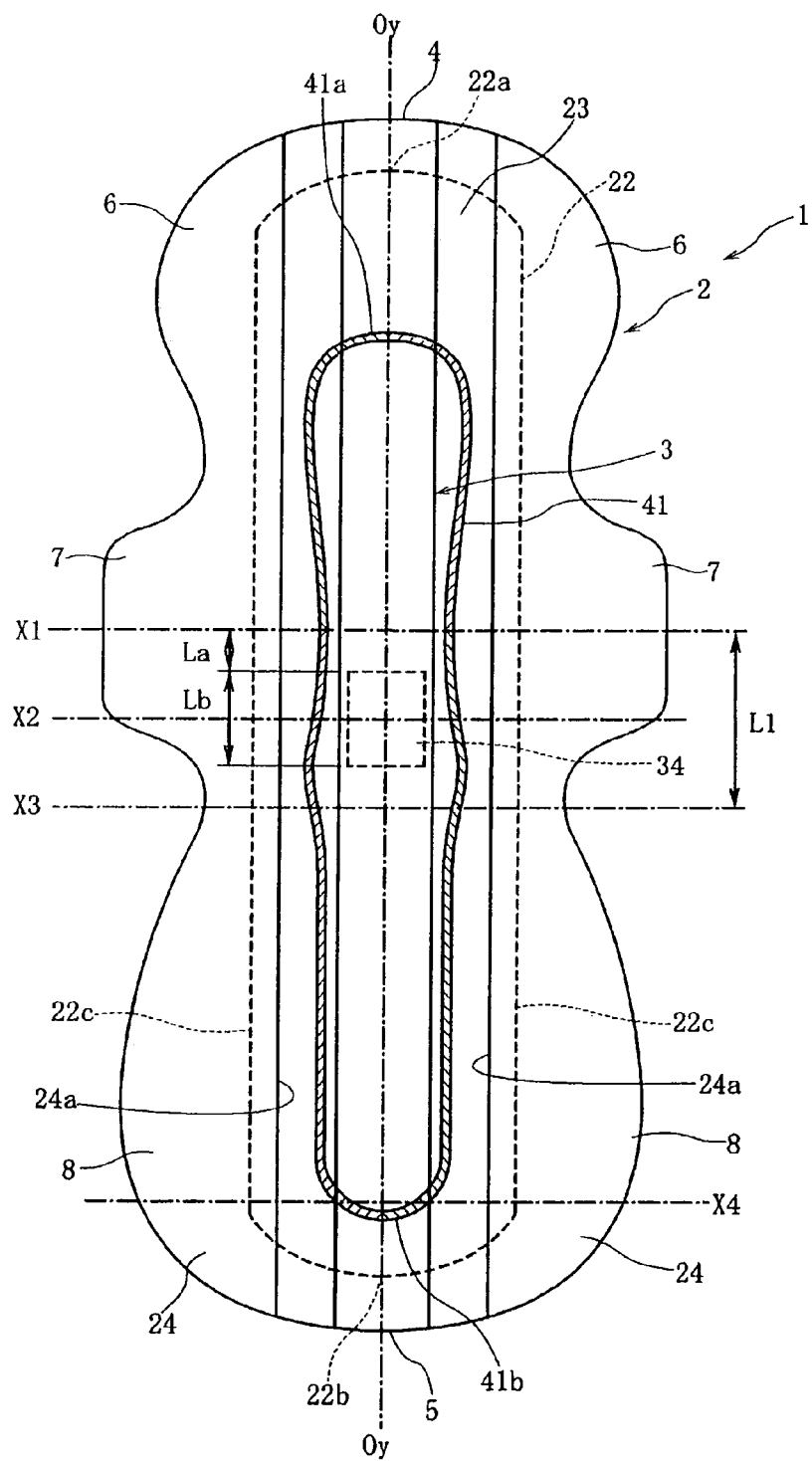
FIG. 2 is a plan view showing a body surface of the sanitary napkin of FIG. 1 in a flattened state.
Figure 3:
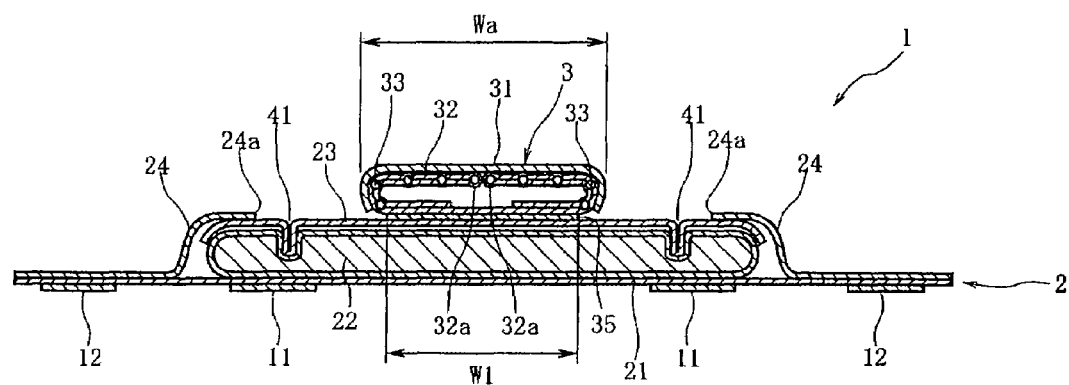
FIG. 3 is a sectional view taken along line III-III of FIG. 1.
Figure 4:
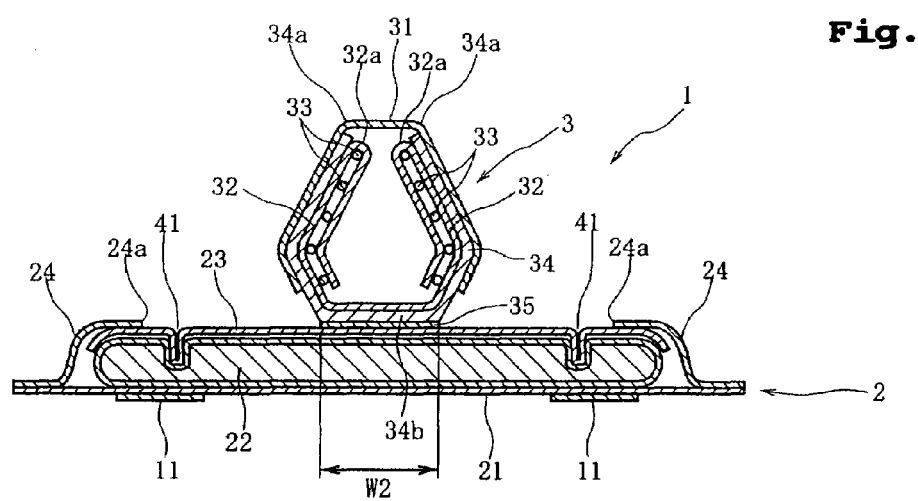
FIG. 4 is a sectional view taken along line IV-IV of FIG. 1.
Figure 5:
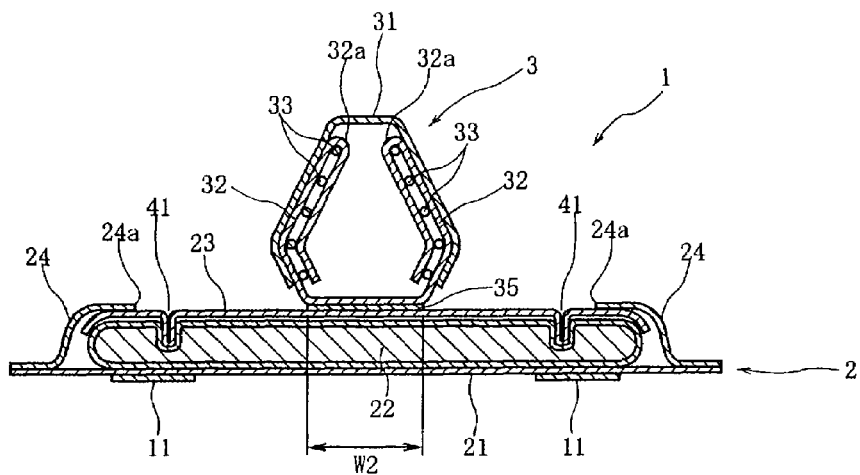
FIG. 5 is a sectional view taken along line V-V of FIG. 1.
Figure 6:
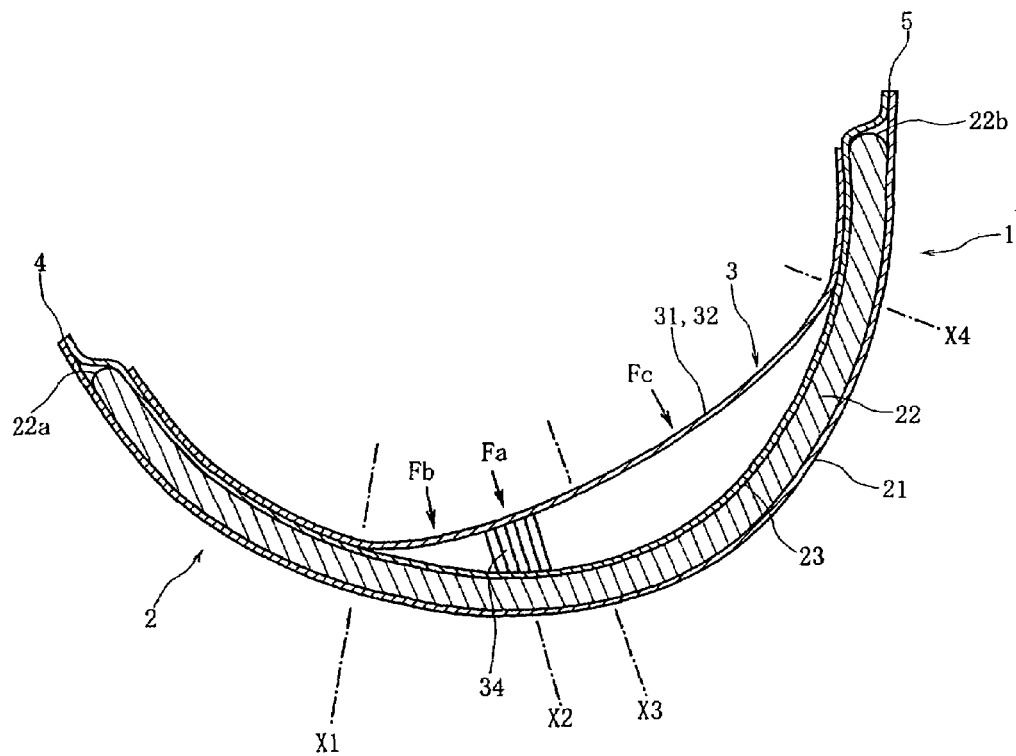
FIG. 6 is a longitudinal sectional view of the sanitary napkin of FIG. 1 in a state where no external force is exerted thereon.
Figure 7:
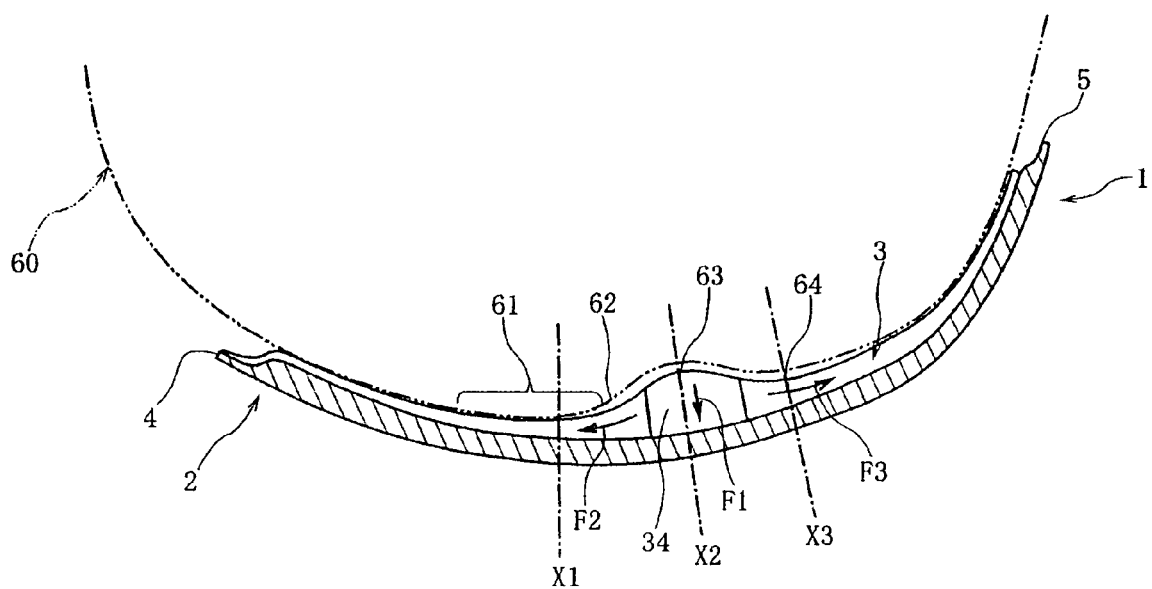
FIG. 7 is a longitudinal sectional view of the sanitary napkin of FIG. 1, schematically showing deformation when a body pressure is exerted thereon during wear.

FIG. 1 is a perspective view of a sanitary napkin according to a first embodiment of the present invention in a state where no external force is exerted thereon. FIG. 2 is a plan view showing a body surface of the sanitary napkin in a flattened state. FIG. 3 is a sectional view taken along line III-III of FIG. 1, FIG. 4 is a sectional view taken along line IV-IV of FIG. 1, and FIG. 5 is a sectional view taken along line V-V of FIG. 1. FIG. 6 is a longitudinal sectional view of the sanitary napkin in a state where no external force is exerted thereon. FIG. 7 is a longitudinal sectional view of the sanitary napkin, schematically showing deformation when a body pressure is exerted thereon during wear.

It should be noted that the sanitary napkin, as well as its individual components, has two major surfaces: of which one surface intended to be worn toward the wearer's crotch is referred to as "body surface", while the other surface is referred to as "garment surface". In addition, the lengthwise direction of the sanitary napkin is referred to as "longitudinal direction", while the direction perpendicular to the longitudinal direction is referred to as "lateral direction". With respect to dimensions of the individual components, unless otherwise stated, a dimension measured in the longitudinal direction is referred to as "length", while a dimension measured in the lateral direction is referred to as "width".

In the following embodiments, the sanitary napkin includes a main body mainly constituted of a liquid-absorbent layer and a backsheet and a projection bulging from the body surface of the main body. The sanitary napkin further includes a topsheet (or cover sheet) which may be adopted only for the main body or for both the main body and the projection.

According to the first embodiment, as shown in FIGS. 1 and 2, a sanitary napkin 1 includes a main body 2 and a projection 3 disposed on the body surface of the main body 2.

As shown in FIGS. 3 to 5, the main body 2 includes a liquid-blocking backsheet 21 lying on the garment surface side of the main body 2, a liquid-absorbent layer 22 disposed on the backsheet 21, a liquid-permeable topsheet 23 covering the liquid-absorbent layer 22, and side sheets 24, 24 lying on the body surface side of the main body 2 and opposite one another in the lateral direction. These components are bonded to each other through a hot-melt type adhesive.

As shown in FIG. 2, the main body 2 has arcuate front and rear edges 4, 5. The main body 2 is elongated to have a length of 280 to 450 mm on a longitudinal centerline Oy. The liquid-absorbent layer 22 is also elongated to have arcuate front and rear edges 22a, 22b, which are spaced slightly inward from the front and rear edges 4, 5, respectively. The liquid-absorbent layer 22 has right and left side edges 22c, 22c, which extend linearly in parallel to the longitudinal centerline Oy. However, the shape of the right and left side edges 22c, 22c of the liquid-absorbent layer 22 should not be understood as limited to this embodiment.

Outside the side edges 22c, 22c of the liquid-absorbent layer 22, the main body 2 has laterally projecting front flaps 6, 6, laterally projecting fold-back flaps 7, 7, and laterally projecting rear flaps 8, 8 in order from front to rear. In the front flaps 6, 6, the fold-back flaps 7, 7, and the rear flaps 8, 8, the side sheets 24 are laid on and bonded to the backsheet 21 through a hot-melt type adhesive.

The side sheets 24, 24 lie opposite one another in the lateral direction with their opposing edges 24a, 24a located inside the side edges 22c, 22c of the liquid-absorbent layer 22 (i.e., located closer to the longitudinal centerline Oy than the side edges 22c, 22c). At the laterally opposite side portions of the liquid-absorbent layer 22, as shown in FIGS. 3 to 5, the body surface of the liquid-absorbent layer 22 is covered with the topsheet 23, and the body surface of the topsheet 23 is further covered with the side sheets 24, 24. In the area defined between the opposing edges 24a, 24a of the side sheets 24, 24, the liquid-permeable topsheet 23 is exposed externally. The overlap between this area and the liquid-absorbent layer 22 is called "main liquid-absorbent region".

X1 shown in FIGS. 1 and 2 represents a vagina-facing reference line, and FIG. 3 is a sectional view of the sanitary napkin 1 taken along the vagina-facing reference line X1. The vagina-facing reference line X1 is spaced 100 to 200 mm, preferably 100 to 140 mm, for example, about 120 mm, rearward from the front edge 4 of the main body 2.

The intersection of the vagina-facing reference line X1 and the longitudinal centerline Oy is called "vagina-facing reference position". The vagina-facing reference position is a target position with which the center of the vaginal opening is to almost coincide when wearing the sanitary napkin 1 along with an undergarment. Leading to this target is through the contour of the sanitary napkin as viewed from the body surface side or the whole design including the arrangement of compression line 41 on the body surface. Particularly when the fold-back flaps 7, 7 are provided as in the present embodiment, the vagina-facing reference line X1 usually coincides with the longitudinal centers of the fold-back flaps 7, 7. Also in the present embodiment, the lateral distance between right and left side portions of the compression line 41 is reduced on the vagina-facing reference line X1 to facilitate positioning of the sanitary napkin 1.

X3 shown in FIGS. 1 and 2 represents an anus-facing reference line and FIG. 5 is a sectional view of the sanitary napkin 1 taken along the anus-facing reference line X3. The anus-facing reference line X3 is intended to face the anus when the vagina-facing reference line X1 coincides with the center of the vaginal opening. The anus-facing reference line X3 is usually spaced a distance L1 of 30 to 70 mm, which varies depending on the wearer's body, rearward from the vagina-facing reference line X1.

Between the vagina-facing reference line X1 and the anus-facing reference line X3, there is set a perineum-facing reference line X2. FIG. 4 is a sectional view of the sanitary napkin 1 taken along the perineum-facing reference line X2. The perineum-facing reference line X2 is intended to face the perineum located between the posterior commissure of labia majora and the anus when the vagina-facing reference line X1 coincides with the center of the vaginal opening.

Behind the anus-facing reference line X3, the sanitary napkin 1 is intended to face the wearer's body from the intergluteal cleft to the coccyx.

As shown in FIGS. 3 to 5, the projection 3 has a projection topsheet 31, an interior sheet 32 covered with the projection topsheet 31, and a plurality of elastic members 33 for exerting a longitudinal elastic contractive force.

The interior sheet 32 is a single hydrophilic and liquid-permeable sheet. On both sides of the longitudinal centerline Oy, the interior sheet 32 is folded back and the same number of elastic members 33 are held between confronting faces of the folded interior sheet 32. The confronting faces of the folded interior sheet 32, as well as the elastic members 33 held therebetween, are bonded to each other through a hot-melt type adhesive that is applied in such an amount as not to interfere with passage of liquid. The elastic members 33 are bonded to the interior sheet 32 while being stretched at least 1.2 times the original length so as to exert a longitudinal elastic contractive force on the projection 3.

Right and left fold lines 32a, 32a of the interior sheet 32 are spaced from the body surface of the main body 2 on both sides of the longitudinal centerline Oy. The projection topsheet 31 is provided to cover the interior sheet 32. The outer surface of the interior sheet 32 is bonded to the inner surface of the projection topsheet 31 through a hot-melt type adhesive that is applied in such an amount as not to interfere with passage of liquid. The projection topsheet 31 thus provided extends between the fold lines 32a, 32a to connect the right and left portions of the interior sheet 32.

On the perineum-facing reference line X2, as shown in FIG. 4, a stiffening member 34 is provided inside the projection 3. The stiffening member 34 is disposed between the outer surface of the interior sheet 32 and the inner surface of the projection topsheet 31. The stiffening member 34 is bonded to both the interior sheet 32 and the projection topsheet 31 through a hot-melt type adhesive that is applied in such an amount as not to interfere with passage of liquid. The stiffening member 34 have opposite edges 34a, 34a, which almost coincide with the fold lines 32a, 32a of the interior sheet 32, and a bottom portion 34b, which is sandwiched between the topsheet 23 of the main body 2 and the interior sheet 32.

As shown in FIG. 2, the stiffening member 34 does not lie on the vagina-facing reference line X1 and is disposed behind the vagina-facing reference line X1 and in front of the anus-facing reference line X3. However, it is also possible to dispose the stiffening member 34 on the anus-facing reference line X3. The distance La between the front end of the stiffening member 34 and the vagina-facing reference line X1 may be, for example, 20 to 40 mm, and the length Lb of the stiffening member 34 may be, for example, 20 to 50 mm.

In a front area between the front edge 4 and the vagina-facing reference line X1 or the vicinity thereof, as shown in FIG. 3, the interior sheet 32 is bonded to the topsheet 23 of the main body 2 through a hot-melt type adhesive 35 that is applied in such an amount as not to interfere with passage of liquid. In this front area, the interior sheet 32 and the main body 2 have a sufficiently large bond width W1 to keep the projection 3 folded almost flat on the body surface of the main body 2. Also in a rear area between the rear edge 5 and a rear rising reference line X4 shown in FIG. 2, the interior sheet 32 of the projection 3 and the main body 2 has the sufficiently large bond width W1. In the front and rear areas, the projection 3 is kept almost flat, but the interior sheet 32 may be bonded or unbonded to itself within the projection 3. The flattened projection 3 has a width Wa in the range of about 15 to 40 mm, for example, 26 mm.

Between the vagina-facing reference line X1 and the rear rising reference line X4, as shown in FIGS. 4 and 5, the projection 3 and the main body 2, which are bonded to each other through the hot-melt type adhesive 35 that is applied in such an amount as not to interfere with passage of liquid, have a bond width W2 that is set smaller than the bond width W1 in the front and rear areas. The bond width W2 may be in the range of ⅓ to ⅔ of the bond width W1. For example, the bond width W1 may be 20 mm, and the bond width W2 may be 10 mm.

Of the projection 3, the portion provided with the stiffening member 34 is referred to as "resistive portion", while the portions in front of and behind the resistive portion is referred to as "front and rear flexible portions". In the resistive portion, the stiffening member 34 and the topsheet 23 of the main body 2 are bonded to each other through the holt-melt type adhesive 35. In the front and rear flexible portions, on the other hand, the interior sheet 32 and the topsheet 23 of the main body 2 are bonded to each other through the holt-melt type adhesive 35.

The individual elastic members 33 extend continuously at least between the vagina-facing reference line X1 and the rear rising reference line X4. The elastic members 33 exert a longitudinal elastic contractive force to bring the vagina-facing reference line X1 and the rear rising reference line X4 closer to each other. When no external force is exerted on the sanitary napkin 1, therefore, the main body 2 is longitudinally curved with its body surface recessed between the vagina-facing reference line X1 and the rear rising reference line X4, which raises the projection 3 away from the body surface of the main body 2. Here, the projection 3 has a front rising end on or near the vagina-facing reference line X1 and a rear rising end on or near the rear rising reference line X4.

As shown in FIGS. 1 and 2, the body surface of the sanitary napkin 1 has the compression line 41 which is formed by pressing and heating the topsheet 23 and the liquid-absorbent layer 22 together. In the front and rear areas of the sanitary napkin 1, front and rear end portions 41a, 41b of the compression line 41 extend across the projection 3. In these overlaps, the interior sheet 32 and projection topsheet 31 of the projection 3 are pressed together with the topsheet 23 and liquid-absorbent layer 22 of the main body 2.

The compression line 41 is formed to enclose an elongated area where the liquid-absorbent layer 22 is present. The compression line 41 increases the stiffness of the main body 2, inhibiting the occurrence of folds in the main body 2 subjected to the elastic contractive force of the elastic members 33 between the vagina-facing reference line X1 and the rear rising reference line X4. This enables longitudinal uniform curvature of the main body 2.

As shown in FIGS. 3 and 5, the main body 2 has pressure-sensitive adhesive layers 11 on the garment surface of the backsheet 21 for securement to an undergarment. The pressure-sensitive adhesive layers 11 extend in the form of strips on both sides of and in parallel to the longitudinal centerline Oy. For the fold-back flaps 7, 7, the main body 2 also has pressure-sensitive adhesive layers 12 on the garment surface of the backsheet 21, as shown in FIG. 3.

Now there will be described preferred materials for the sanitary napkin 1 according to the first embodiment of the present invention.

The backsheet 21 of the main body 2 may be a polyethylene film having a basis weight of 23 g/m². The liquid-absorbent layer 22 may be a mixture of softwood kraft pulp and superabsorbent polymer wrapped in a hydrophilic tissue. The superabsorbent polymer content may be about 3% by weight of the liquid-absorbent layer 22. The basis weight of the liquid-absorbent layer 22 may be either uniform or higher in the area enclosed by the compression line 41 or the overlap of the area enclosed by the compression line 41 and the area in front of the anus-facing reference line X3 than in the other area. For example, the overlap of the area enclosed by the compression line 41 and the area in front of the anus-facing reference line X3 may have a basis weight of 800 g/m² and the other area may have a basis weight of 450 g/m².

The topsheet 23 of the main body 2 may be a hydrophilic and liquid-permeable nonwoven fabric or a resin film with a large number of apertures for passage of liquid. For example, the topsheet 23 may be a through-air bonded nonwoven fabric manufactured by bonding synthetic resin fibers through a hot air, wherein the synthetic resin fibers may be 2.2 dtex sheath/core bicomponent fibers of which the core is polyester and the sheath is polyethylene. The topsheet 23 may have a basis weight of about 20 g/m². The side sheet 24 may be a spun-bonded nonwoven fabric manufactured from sheath/core bicomponent fibers of which the core is polypropylene and the sheath is polyethylene. For example, the side sheet 24 may have a basis weight of about 22 g/m².

Of the components constituting the projection 3, the projection topsheet 31 and interior sheet 32 may be a hydrophilic, liquid-permeable and longitudinally stretchable nonwoven fabric. For example, these sheets may be formed of the same through-air bonded nonwoven fabric as the topsheet 23. The elastic members 33 may be polyurethane elastic filaments having a fineness of about 940 dtex. These polyurethane elastic filaments may be secured to the interior sheet 32 while being stretched 1.4 times the original length.

Figure 8A:
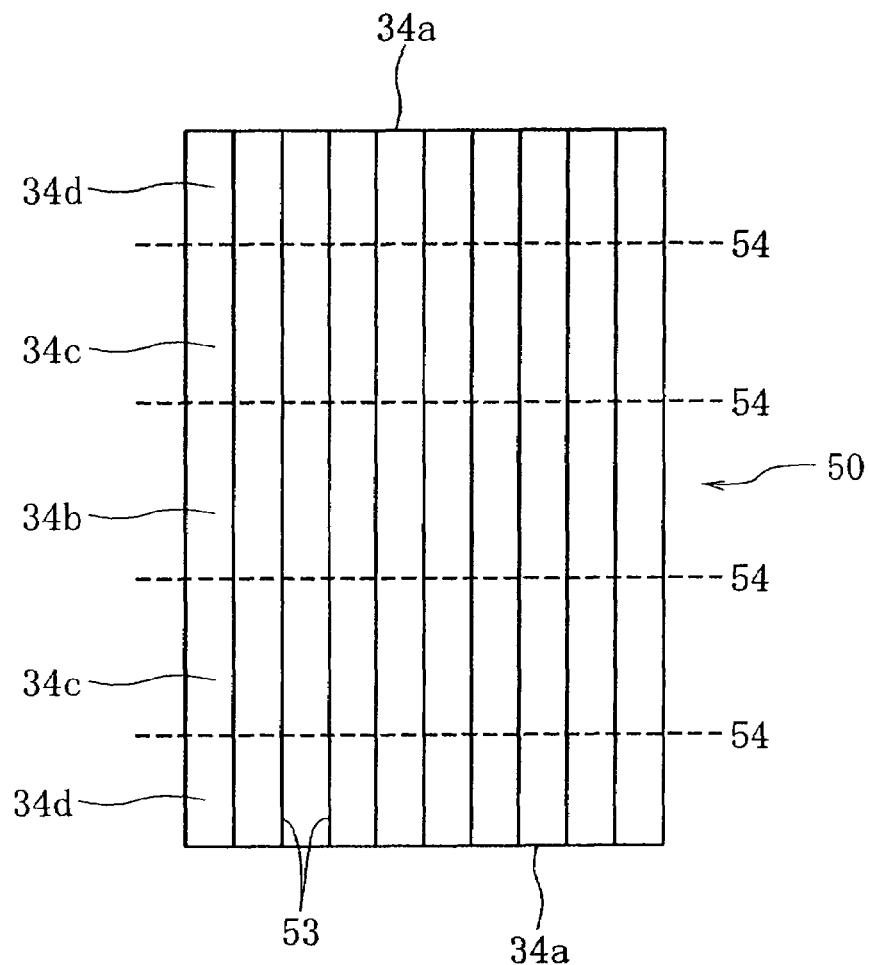
FIG. 8(A) is a plan view of a stiff sheet forming a stiffening member.
Figure 8B:
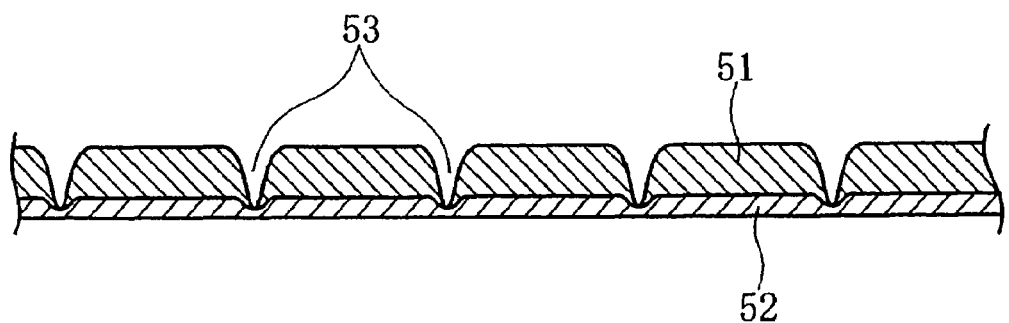
FIG. 8(B) is a sectional view of the stiff sheet of FIG. 8(A)
Figure 9:
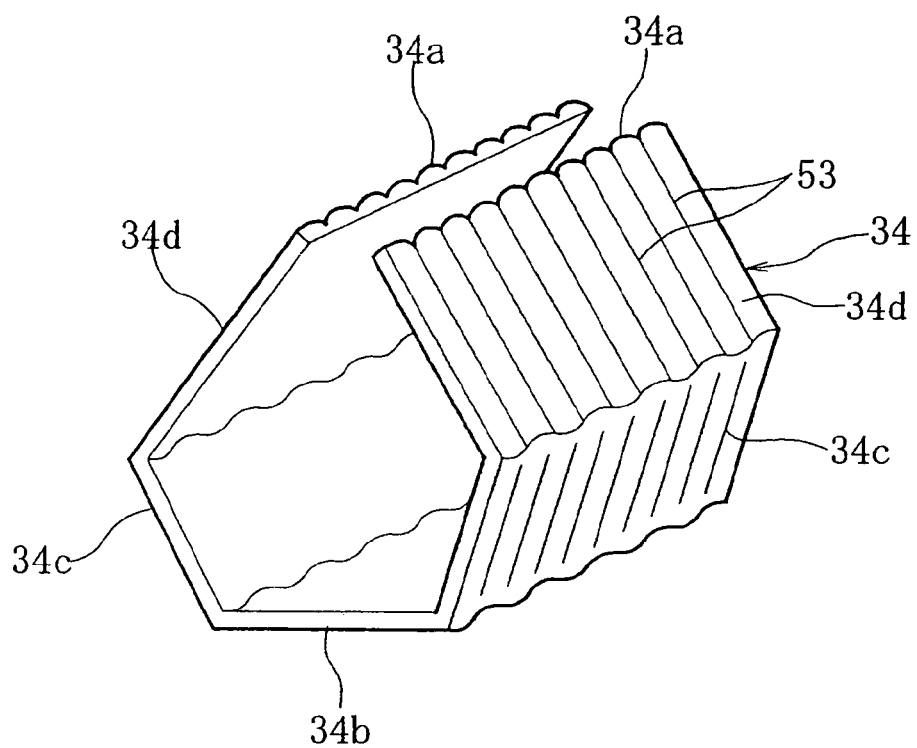
FIG. 9 is a perspective view of the stiffening member.

FIG. 9 shows the stiffening member 34 which is also a component of the projection 3. The stiffening member 34 is formed by folding a stiff sheet 50 shown in FIGS. 8(A) and 8(B). The stiffening member 34 has the edges 34a, 34a, which are spaced apart from the main body 2 and opposed to each other across the longitudinal centerline Oy, the bottom portion 34b, which is bonded to the main body 2, lower rising walls 34c, 34c, which are folded upward from the bottom portion 34b, and upper rising walls 34d, 34d.

The stiff sheet 50 constituting the stiffening member 34 may be formed by laminating a plurality of sheets to have a higher bending stiffness than the laminate of the projection topsheet 31 and the interior sheet 32. As shown in FIG. 8(B), the stiff sheet 50 may have a first layer 51 and a second layer 52. The first layer 51 may be a hydrophilic air-laid nonwoven fabric manufactured by depositing 70 wt. % of pulp fibers and 30 wt. % of synthetic resin fibers by air-laid process, pressing them into a flat sheet, and bonding them together through an acrylic binder. Alternatively, the first layer 51 may be an air-laid pulp manufactured only from pulp fibers in the same manner as described above. The first layer 51 may have a basis weight of about 40 g/m². The second layer 52 may be a hydrophilic nonwoven fabric, e.g., a through-air bonded nonwoven fabric manufactured from 4.4 dtex sheath/core bicomponent fibers of which the core is polypropylene and the sheath is polyethylene. The second layer 52 may have a basis weight of about 25 g/m². The fibers constituting the second layer 52 have a larger fineness than the fibers constituting the projection topsheet 31 and the interior sheet 32. As a result, the second layer 52 has a higher bending stiffness than the projection topsheet 31 and the interior sheet 32.

After bonded through a hot-melt type adhesive, the first and second layers 51, 52 are partially compressed to have compression lines 53 in the surface of the first layer 51. The compression lines 53 alternate with uncompressed portions. On fold lines 54 crossing the compression lines 53, the second layer 52 is folded inward to provide the stiffening member 34 shown in FIG. 9. In an alternative to the compression lines 53, the stiff sheet 50 may be formed with dotted compression portions.

FIG. 6 is a longitudinal sectional view of the sanitary napkin 1 taken along the longitudinal centerline Oy. Since the elastic members 33 exert a longitudinal elastic contractive force between the vagina-facing reference line X1 and the rear rising reference line X4, the main body 2 under no external force is concavely curved to raise the projection 3 from the body surface of the main body 2 between the vagina-facing reference line X1 and the rear rising reference line X4. The projection 3 thus raised is hollow, as shown in FIGS. 4, 5 and 6.

The stiffening member 34 lies on the perineum-facing reference line X2 to function as a resistive member. When Fa represents a force required to depress the projection 3 toward the main body 2 by a predetermined distance at a longitudinal midpoint of the stiffening member 34, Fb represents a force required to depress the projection 3 toward the main body 2 by a predetermined distance at a midpoint between the front end of the stiffening member 34 and the vagina-facing reference line X1, and Fc represents a force required to depress the projection 3 toward the main body 2 by a predetermined distance at a midpoint between the rear end of the stiffening member 34 and the rear rising reference line X4, Fa is greater than Fb and Fc and preferably at least 1.2 times, more preferably at least 1.5 times of Fb and Fc. It is also preferred that Fa>Fb>Fc.

Preferably, Fa is in the range of 0.2 to 4.0 N, wherein the projection 3 is depressed such that the rising height of the projection 3 from the body surface of the main body 2 is reduced to 80% of the original height under no external force (or 20% depression). This measurement may be carried out using a measurement device with a cylindrical surface having a radius of curvature of 110 mm. The backsheet 21 of the sanitary napkin 1 shown in FIG. 6 is adhered to the cylindrical surface and curved with a radius of 110 mm. Then, a 30 mm radius circular plane of a measuring pusher of a tensilon tester is applied to the top portion of the projection 3. Fa is a load measured when the top portion of the projection 3 is pushed radially of the cylindrical surface with the measuring pusher to reduce the rising height to 80% of the original height under no external force.

The composite of the projection topsheet 31, the interior sheet 32, and the elastic member 33 is longitudinally stretchable and subjected to a longitudinal elastic contractive force. If the composite is cut into a sample having a width of 25 mm and a length of 75 mm and the sample is held by chucks initially spaced 50 mm apart from each other in the longitudinal direction, it is preferred that a load required to stretch the sample 10 mm (1.2 times the original length) is in the range of 0.1 to 4.0 N. After removal of the tension, it is also preferred that the residual strain is 5% or less for the measurement length of 50 mm.

If the load Fa measured when the projection 3 is pushed to cause 20% depression is in the range of 0.2 to 4.0 N, the stiffening member 34 can be maintained in a three dimensional configuration under body pressure without giving an unpleasant feeling to the wearer's body. If the load required to stretch the composite 1.2 times the original length is in the range of 0.1 to 4.0 N/25 mm and its residual strain is 5% or less, the flexible portions of the projection 3 can be appropriately stretched in the longitudinal direction, conforming to the contour of the wearer's body. Since the projection 3 can be stretched or contracted with increase or decrease of the body pressure, the projection 3 can easily be kept in contact with the wearer's body.

FIG. 7 is a sectional view taken along the longitudinal centerline Oy, showing a state where the sanitary napkin 1 is applied to the crotch of a woman's body 60. In the woman's body 60 shown in FIG. 7, the vaginal opening including the labia majora is indicated by 61, the posterior commissure of labia majora is indicated by 62, the perineum is indicated by 63, and the anus is indicated by 64.

Of the projection 3, the resistive portion shown in FIG. 4 is intended to come into contact with a shallow recess of the woman's body 60 at or near the perineum 63; the flattened portion shown in FIG. 3 is intended to come into contact with the vaginal opening 61; and the rear flexible portion shown in FIG. 5 is intended to come into contact with the anus 64 and the intergluteal cleft behind the anus 64.

At the resistive portion facing the perineum 63, the rising walls of the projection 3 are stiffened by the lower and upper rising walls 34c, 34d of the stiffening member 34. This prevents the projection 3 from easily collapsing under a body pressure F1, thereby keeping the resistive portion in contact with the perineum 63. Since the stiffening member 34 resists collapsing, the projection 3 does not easily collapse even when the body pressure acts in front of the stiffening member 34. Here, the front flexible portion of the projection 3 is in contact with the woman's body 60 while receiving a tensile force F2 due to the body pressure. That is, the composite constituting the front flexible portion can easily conform to the contour of the woman's body 60, ensuring contact with the vaginal opening 61. Also behind the stiffening member 34, the rear flexible portion of the projection 3 is in contact with the woman's body 60 at or near the anus 64 while receiving a tensile force F3 due to the body pressure. That is, when the projection 3 is subjected to a body pressure, the front and rear flexible portions of the projection 3 can be stretched forward and rearward from the stiffening member 34, which ensures that the projection 3 will be kept in contact with the wearer's body not only at the resistive portion but also at the front and rear flexible portions.

In addition, since the stiffening member 34 locally increases the bending stiffness of the sanitary napkin 1, the sanitary napkin 1 can be curved such that the areas in front of and behind the stiffening member 34 conform to the contour of the wearer's body while the area provided with the stiffening member 34 functions as a fulcrum, as shown in FIG. 7. This prevents undesirable folding of the sanitary napkin 1, for example, at the vagina-facing reference position, as well as twisting of the sanitary napkin 1, thereby ensuring contact of the while sanitary napkin 1 with the wearer's body.

Moreover, since the stiffening member 34 has a plurality of the compression lines 53 that are perpendicular to the longitudinal direction, as shown in FIG. 9, the stiffening member 34 can be slightly deformed to contract in the longitudinal direction in accordance with the curvature of the main body 2. This is effective in preventing the stiffening member 34 from giving an unpleasant feeling to the wearer's body.

Since the projection 3 of the sanitary napkin 1 can be kept in contact with the wearer's body from the vaginal opening 61, through the posterior commissure of labia majora 62 and the perineum 63, to the anus 64, wastes discharged from the vaginal opening 61 can be reliably collected by the projection 3 and transferred to the underlying liquid-absorbent layer 22. This is effective in preventing lateral leakage of menstrual blood or rearward leakage of menstrual blood in a sleeping or sitting position.

In the first embodiment, it is not necessarily required to provide the projection 3 with the elastic members 33. In order to raise the projection 3 from the body surface of the main body 2, for example, at least one of the projection topsheet 31 and the interior sheet 32 may be formed of a nonwoven fabric which is capable of exerting a sufficient longitudinal elastic contractive force to curve the main body 2, as shown in FIG. 6. In the structure shown in FIG. 4, it is also possible to dispose the stiffening member 34 inside the interior sheet 32.

Figure 10:
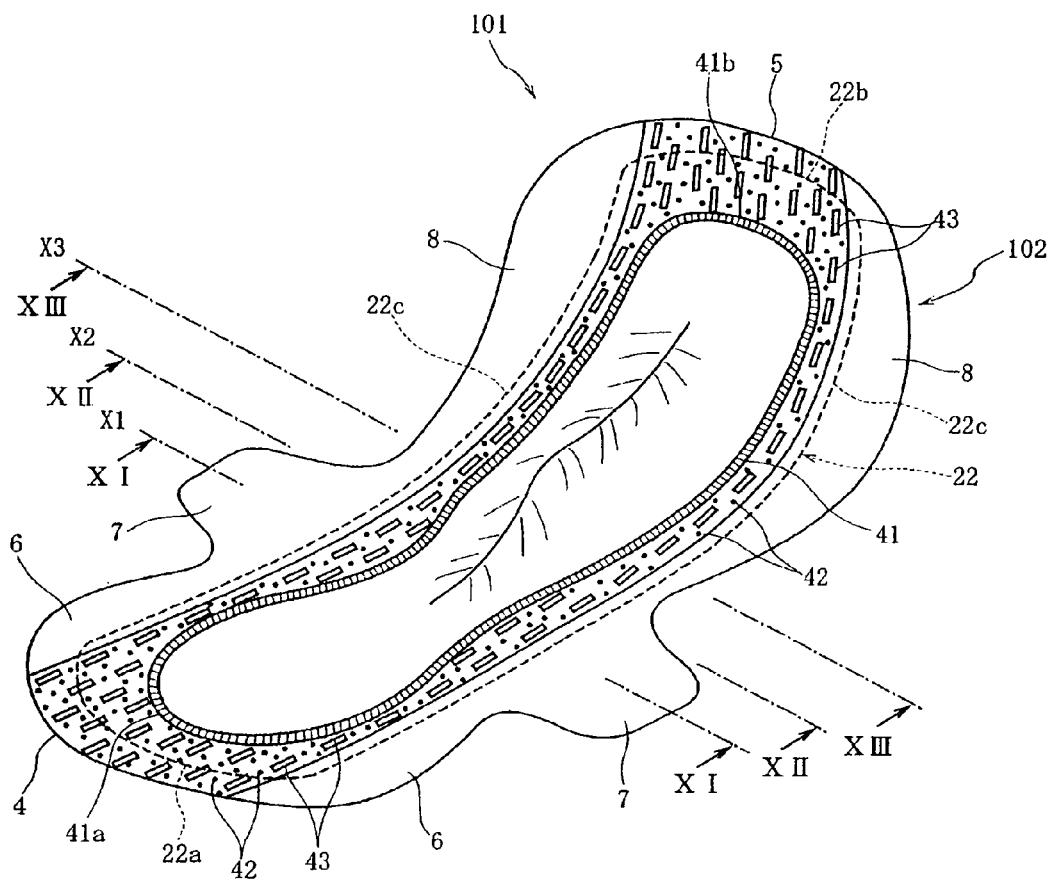
FIG. 10 is a perspective view of a sanitary napkin according to a second embodiment of the present invention in a state where no external force is exerted thereon.
Figure 11:
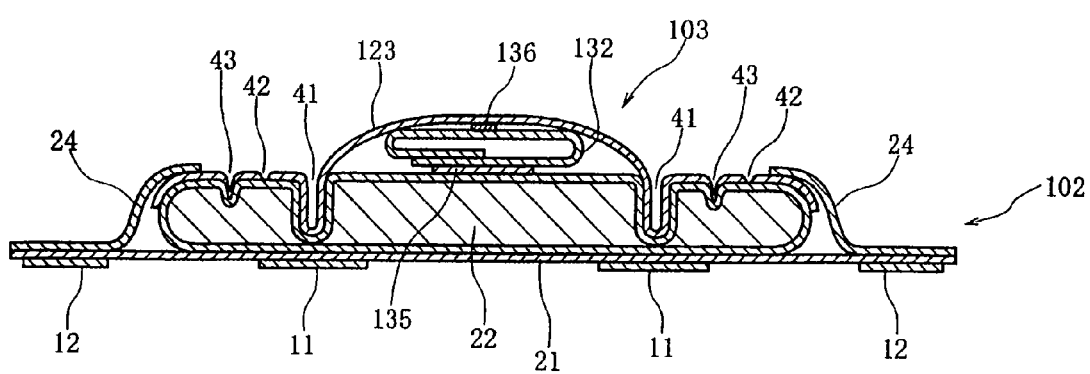
FIG. 11 is a sectional view taken along line XI-XI of FIG. 10.
Figure 12:
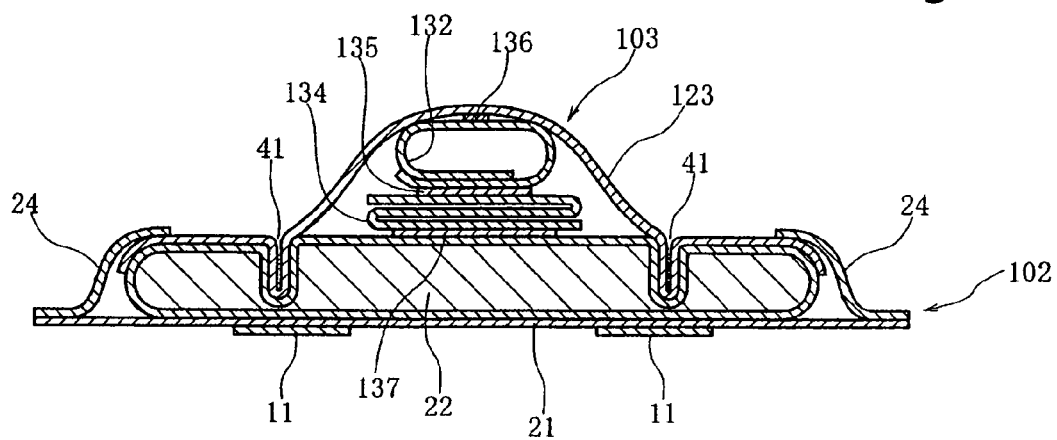
FIG. 12 is a sectional view taken along line XII-XII of FIG. 10.
Figure 13:
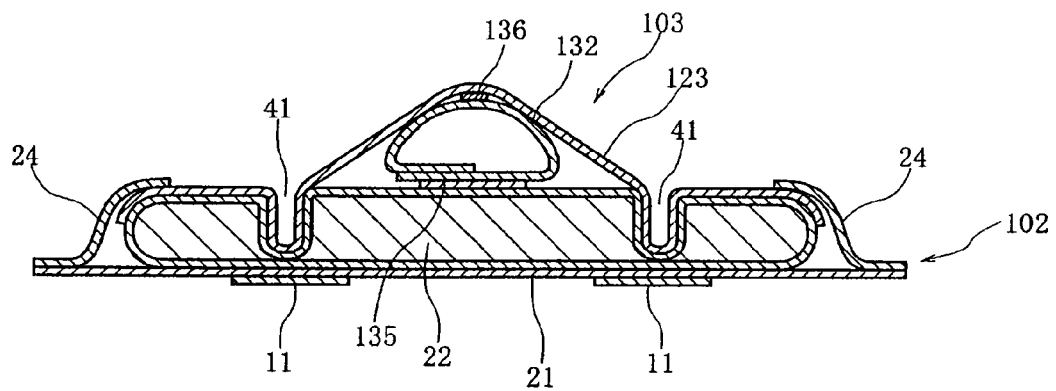
FIG. 13 is a sectional view taken along line XIII-XIII of FIG. 10.
Figure 14:
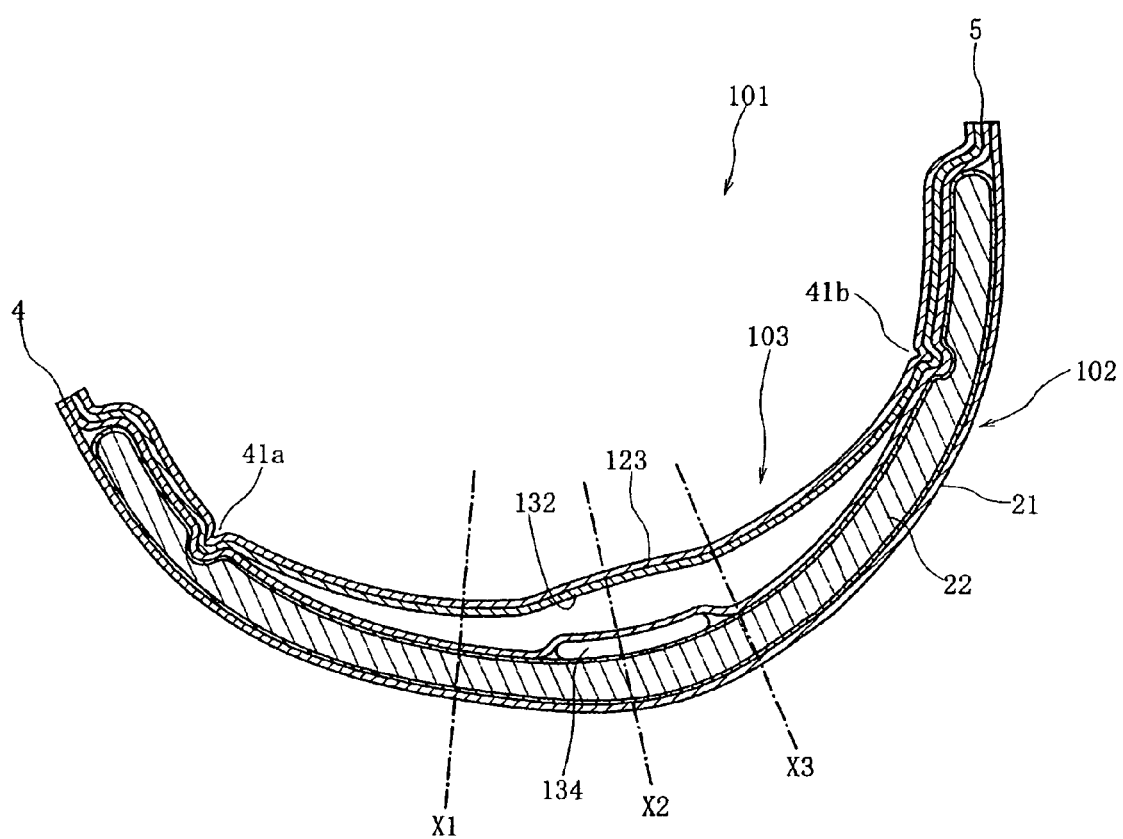
FIG. 14 is a longitudinal sectional view of the sanitary napkin of FIG. 10 in a state where no external force is exerted thereon.
Figure 15:
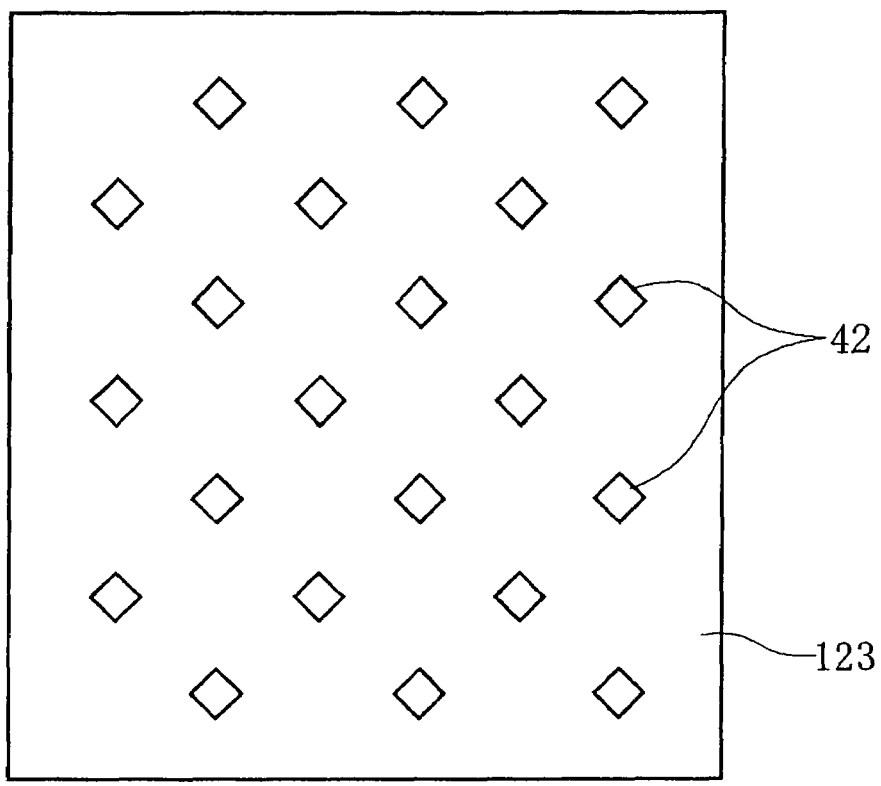
FIG. 15 is a schematic diagram showing an embossment pattern formed by pressing a cover sheet.
Figure 16:
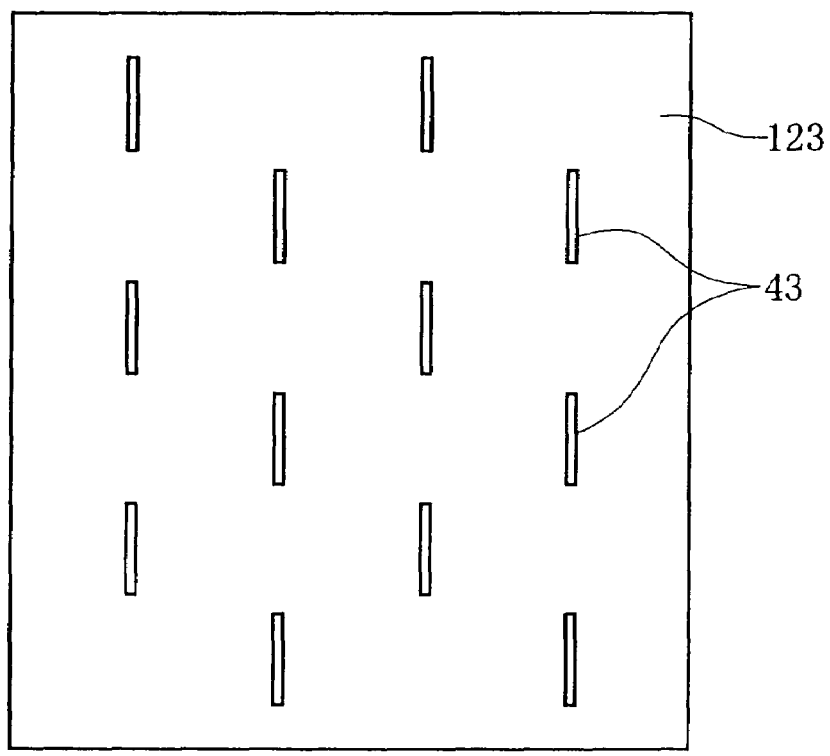
FIG. 16 is a schematic diagram showing an embossment pattern formed by pressing a cover sheet and a liquid-absorbent layer.

FIG. 10 is a perspective view of a sanitary napkin 101 according to a second embodiment of the present invention in a state where no external force is exerted thereon. FIG. 11 is a sectional view taken along line XI-XI of FIG. 10, FIG. 12 is a sectional view taken along line XII-XII of FIG. 10, and FIG. 13 is a sectional view taken along line XIII-XIII of FIG. 10. FIG. 14 is a longitudinal sectional view of the sanitary napkin 101 taken along the longitudinal centerline Oy in a state where no external force is exerted thereon. FIGS. 15 and 16 are schematic diagram showing emboss patterns on a cover sheet. In the sanitary napkin 101 according to the second embodiment, the detailed description of the portions having the same construction as those of the sanitary napkin 1 according to the first embodiment will be omitted by designating them by the common reference numerals.

FIG. 10 shows the vagina-facing reference line X1, perineum-facing reference line X2 and anus-facing reference line X3. FIG. 11 is a sectional view taken along the vagina-facing reference line X1, FIG. 12 is a sectional view taken along the perineum-facing reference line X2, and FIG. 13 is a sectional view taken along the anus-facing reference line X3.

As shown in FIGS. 11 to 13, a main body 102 includes the backsheet 21, the liquid-absorbent layer 22, and the pressure-sensitive adhesive layers 11, 12 disposed on the garment surface of the backsheet 21. On the body surface of the main body 102, a projection 103 extends along the longitudinal centerline Oy.

The sanitary napkin 101 includes a cover sheet 123 that is disposed on the body surface side of the main body 102 and the projection 103. In the second embodiment, the cover sheet 123 forms not only a part of the main body 102 but also a part of the projection 103.

The cover sheet 123 is capable of exerting an elastic contractive force at least in the longitudinal direction. The cover sheet 123 may be a nonwoven fabric including crimped fibers as stretchable fibers, for example, a through-air bonded nonwoven fabric. The crimped fibers may be side-by-side bicomponent fibers manufactured by combining two synthetic resin components with different melting points, for example, 2.2 dtex synthetic resin fibers manufactured by combining two polyethylene components with different melting points. The through-air bonded nonwoven fabric may be manufactured by mixing 70 wt. % of the side-by-side bicomponent fibers and 30 wt. % of polyethylene/polypropylene sheath/core bicomponent fibers and then fusion-bonding the fibers through a hot air. The through-air bonded nonwoven fabric may be used for the cover sheet 123 after being thermally shrunken to 30% of the original length by a heat treatment which develops crimp in the side-by-side bicomponent fibers. After the thermal shrinkage, the basis weight may be, for example, 30 g/m$^2$.

When the cover sheet 123 has a width of 25 mm and a measurement length of 50 mm, it is preferred that the load required to stretch it 1.2 times the original length is in the range of 0.1 to 4.0 N and the residual strain after removal of tension is 5% or less for the measurement length of 50 mm, as in the first embodiment.

With the main body 102 being kept flat, the cover sheet 123 may be laid on the liquid-absorbent layer 22 while being stretched 1.15 times the original length. In the compression line 41 shown in FIG. 10, the cover sheet 123 is heated and pressed together with the liquid-absorbent layer 22. Thus, the cover sheet 123 and the liquid-absorbent layer 22 are secured to each other in the compression line 41.

Outside the area enclosed by the compression line 41, the cover sheet 123 is formed with an emboss pattern 42 shown in FIG. 15 while being stretched 1.15 times the original length. In the individual embossments, the fibers constituting the cover sheet 123 are fusion-bonded under heat and pressure. Outside the area enclosed by the compression line 41, furthermore, the cover sheet 123 is heated and pressed together with the liquid-absorbent layer 22 to have an emboss pattern 43 shown in FIG. 16. Outside the area enclosed by the compression line 41, accordingly, the emboss pattern 42 shown in FIG. 15 restricts the elastic contractive force of the cover sheet 123 and the emboss pattern 43 shown in FIG. 16 secures the cover sheet 123 to the liquid-absorbent layer 22.

Within the area enclosed by the compression line 41, the cover sheet 123 exerts an elastic contractive force to bring the front and rear end portions 41a, 41b of the compression line 41 closer to each other. When no external force is exerted thereon, as shown in FIG. 14, the main body 102 is longitudinally curved with the body surface recessed between the front and rear end portions 41a, 41b, thereby raising the cover sheet 123 from the body surface of the main body 102 within the area enclosed by the compression line 41.

As shown in FIGS. 11 to 13, the sanitary napkin 101 has a projection-forming member 132 between the liquid-absorbent layer 22 of the main body 102 and the cover sheet 123. The projection-forming member 132 is hydrophilic and permeable to liquid or capable of absorbing and retaining liquid. For example, the projection-forming member 132 may be a laminate of a 60 g/m$^2$ air-laid nonwoven fabric of 70 wt. % softwood kraft pulp and 30 wt. % synthetic resin fibers and a 30 g/m$^2$ spunlaced nonwoven fabric of 1.7 dtex rayon fibers, wherein the air-laid nonwoven fabric and the spunlaced nonwoven fabric may be bonded together through a hot-melt type adhesive applied in such an amount as not to interfere with passage of liquid and further united together by embossing them in a dot or linear pattern.

The projection-forming member 132 is bent into a tube with the spunlaced nonwoven fabric directed outward or inward and then bonded to the body surface of the liquid-absorbent layer 22 through a hot-melt type adhesive 135 with their opposite edges overlapping each other. At its top portion, the projection-forming member 132 is also bonded to the garment surface of the cover sheet 123 through a hot-melt type adhesive 136 applied at a width of about 2 to 10 mm in such a pattern as not to interfere with passage of liquid.

On the perineum-facing reference line X2, as shown in FIG. 12, a stiffening member 134, which functions as a resistive member, is secured between the projection-forming member 132 and the liquid-absorbent layer 22. The stiffening member 134 may be formed of the same stiff sheet 50 as shown in FIGS. 8(A) and 8(B). Accordingly, the stiff sheet 50 may be formed by laminating an air-laid nonwoven fabric and a through-air bonded nonwoven fabric and pressing the laminate to have the compression lines or dotted compression portions. As shown in FIG. 12, the stiffening member 134 may be formed by folding the stiff sheet 50 in two or more. The stiffening member 134 and the projection-forming member 132 are bonded to each other through the hot-melt type adhesive 135; the stiffening member 134 and the liquid-absorbent layer 22 are bonded to each other through a hot-melt type adhesive 137.

The stiffening member 134 is preferably disposed within the same area as the stiffening member 34 of the first embodiment. That is, the stiffening member 134 is intended to face the perineum and optionally the anus behind the posterior commissure of labia majora.

The projection-forming member 132 extends along the longitudinal centerline Oy from the front edge 4 to the rear edge 5. At the front and rear end portions 41a, 41b of the compression line 41, the cover sheet 123, the projection-forming member 132 and the liquid-absorbent layer 22 are pressed all together. In the second embodiment, the projection 103 is formed of the cover sheet 123, the projection-forming member 132 and the stiffening member 134.

The liquid-absorbent layer 22 may be a mixture of softwood kraft pulp and superabsorbent polymer. The liquid-absorbent layer 22 may have a largest basis weight (e.g., 900 g/m$^2$) beneath the stiffening member 134 and a second largest basis weight (e.g., 700 g/m$^2$) between the front end of the stiffening member 134 and the front end portion 41a of the compression line 41. In the other area, the liquid-absorbent layer 22 may have a small basis weight (e.g., 450 g/m$^2$).

In the sanitary napkin 101, since the cover sheet 123 exerts a longitudinal elastic contractive force within the area enclosed by the compression line 41, the main body 102 is concavely curved with its body surface recessed between the front and rear end portions 41a, 41b of the compression line 41. Since the projection-forming member 132 is longitudinally deformable and its top portion is bonded to the cover sheet 123, the longitudinal elastic contractive force exerted by the cover sheet 123 also acts on the projection-forming member 132. Therefore, when the projection 103 rises from the main body 102, the top portion of the projection 103 is concavely curved in accordance with the curvature of the main body 102.

On the vagina-facing reference line X1, as shown in FIG. 11, since the cover sheet 123 is spaced only a short distance away from the main body 102, the tubular projection-forming member 132 is hollow but relatively flat. Behind the vagina-facing reference line X1, since the distance between the cover sheet 123 and the main body 102 becomes relatively large, the internal space of the tubular projection-forming member 132 increases due to the resilience of projection-forming member 132.

In the resistive portion provided with the stiffening member 134, as shown in FIG. 12, the projection-forming member 132 is raised by the stiffening member 134 and the liquid-absorbent layer 22 has the largest basis weight beneath the stiffening member 134 to further raise the projection-forming member 132. In the resistive portion, moreover, since the height of the projection-forming member 132 is restricted by the cover sheet 132, the projection-forming member 132 is relatively flat.

In the resistive portion provided with the stiffening member 134, since the projection-forming member 132 is raised by the stiffening member 134 and also relatively flat, as set forth above, 20% depression of the projection 103 toward the main body 102 requires a relatively heavy load. This ensures contact of the resistive portion with the perineum. In the front and rear flexible portions, since the hollow projection-forming member 132 is easy to deform and also subjected to the longitudinal elastic contractive force exerted by the cover sheet 123, the projection-forming member 132 can easily conform to the vaginal opening, the anus, and the intergluteal cleft, ensuring contact with these parts. Also in the second embodiment, therefore, the projection 103 can be kept in contact with the wearer's body at both the resistive and flexible portions.

In the sanitary napkin 101, moreover, the area provided with the stiffening member 134 has a higher bending stiffness than the other area, which ensures independent curvature of the sanitary napkin 101 in front of and behind the stiffening member 134 and effectively prevents folding or twisting of the sanitary napkin 101.

When the projection 103 is in contact with the vaginal opening, menstrual blood discharged from the vaginal opening can be collected by hydrophilicity of the air-laid nonwoven fabric of the projection 103. The collected menstrual blood will pass through or flow down the projection 103 and be then absorbed by the liquid-absorbent layer 22, which eases the anxiety of lateral leakage or rearward leakage of menstrual blood.

Figure 17:
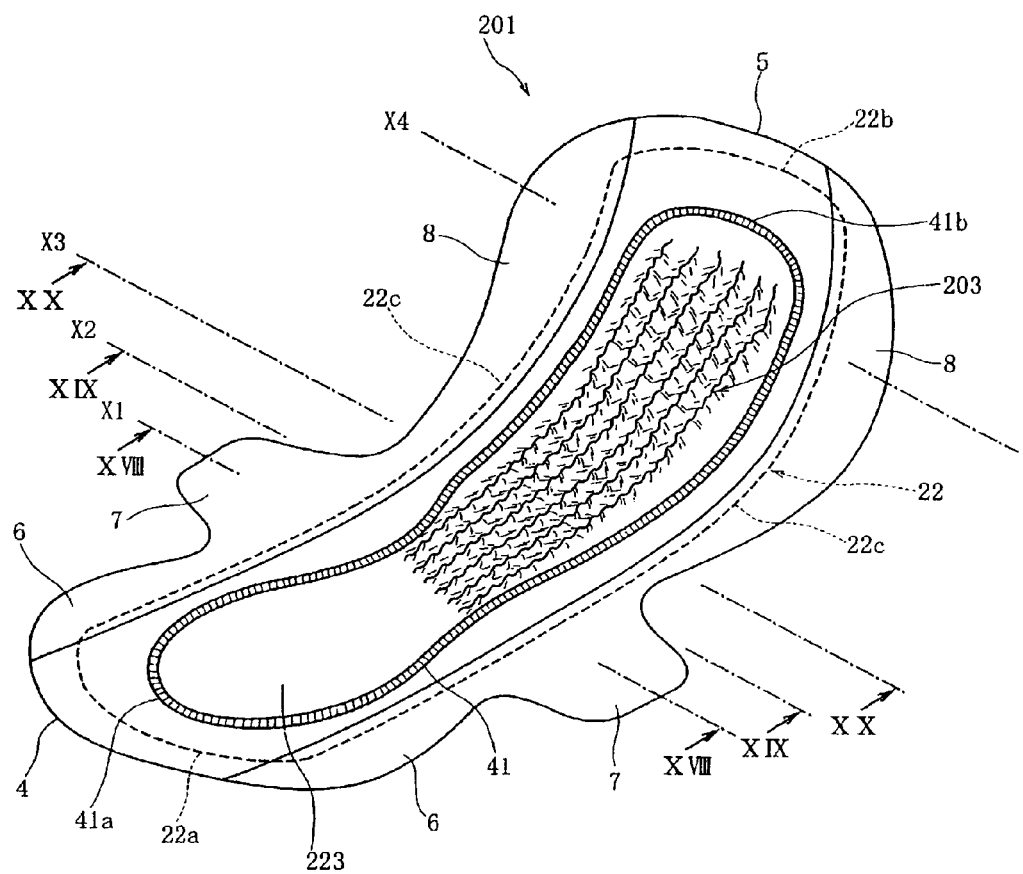
FIG. 17 is a perspective view of a sanitary napkin according to a third embodiment of the present invention in a state where no external force is exerted thereon.
Figure 18:
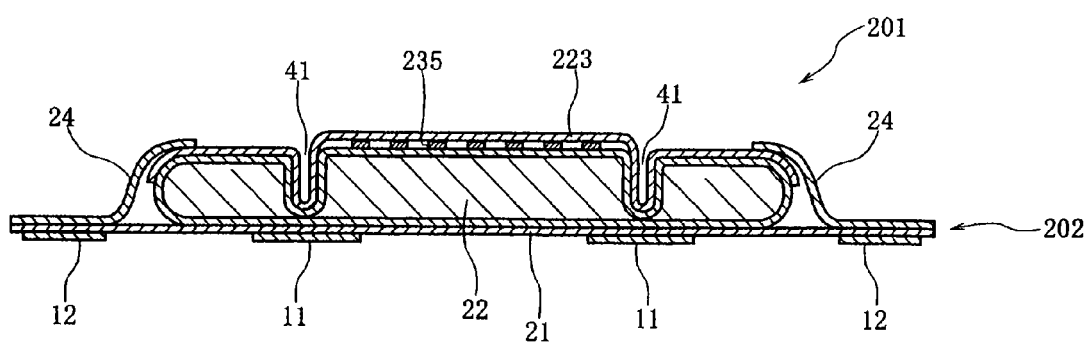
FIG. 18 is a sectional view taken along line XVIII-XVIII of FIG. 17.
Figure 19:
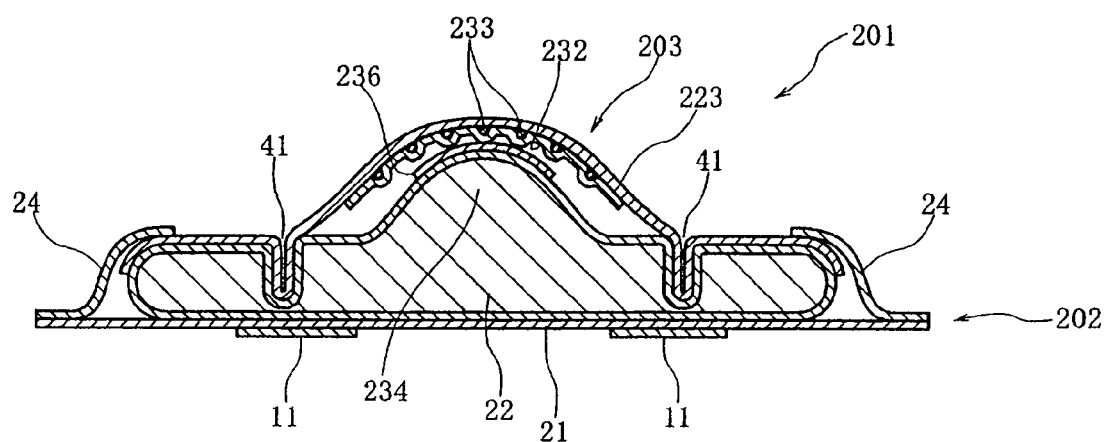
FIG. 19 is a sectional view taken along line XIX-XIX of FIG. 17.
Figure 20:
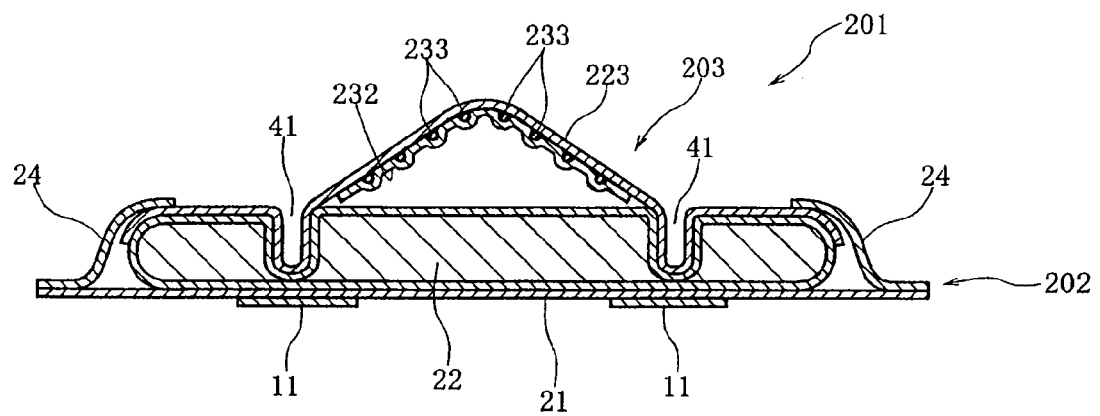
FIG. 20 is a sectional view taken along line XX-XX of FIG. 17.
Figure 21:
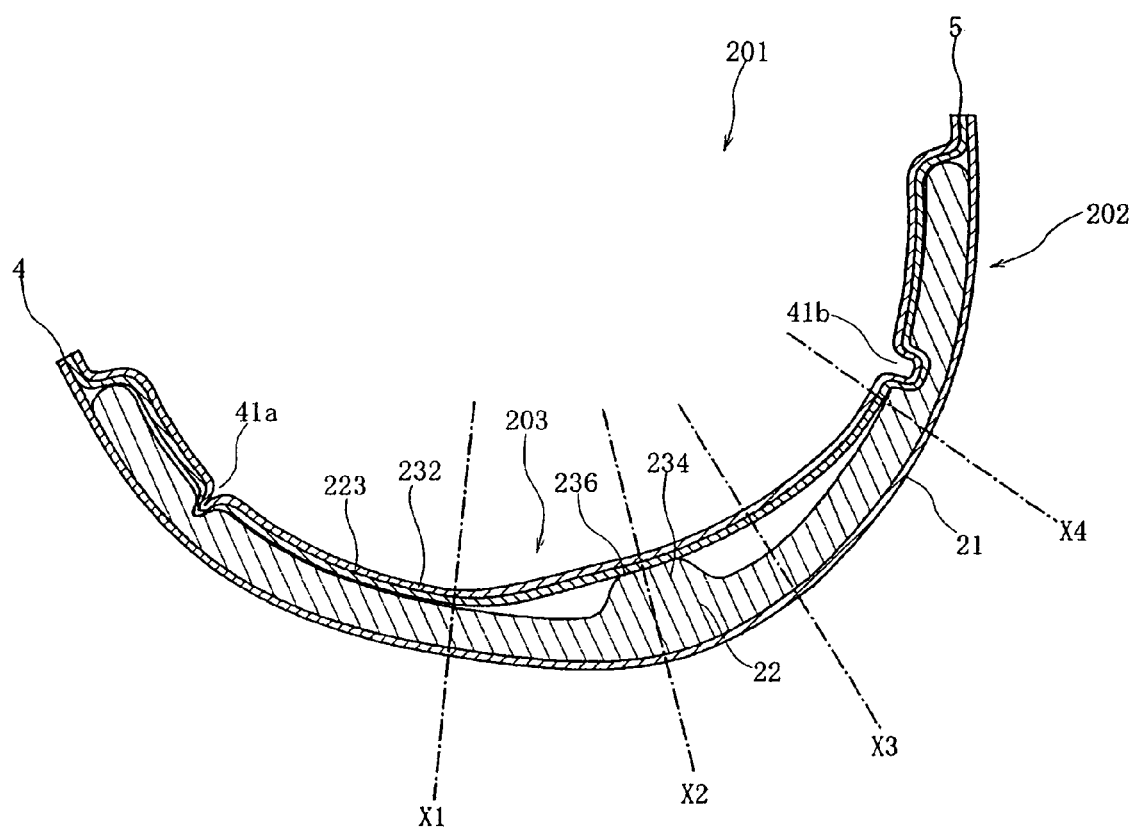
FIG. 21 is a longitudinal sectional view of the sanitary napkin of FIG. 17 in a state where no external force is exerted thereon.

FIG. 17 is a perspective view of a sanitary napkin 201 according to a third embodiment of the present invention in a state where no external force is exerted thereon. FIG. 18 is a sectional view taken along line XVIII-XVIII of FIG. 17, FIG. 19 is a sectional view taken along line XIX-XIX of FIG. 17, and FIG. 20 is a sectional view taken along line XX-XX of FIG. 17. FIG. 21 is a longitudinal sectional view of the sanitary napkin 201 taken along the longitudinal centerline Oy in a state where no external force is exerted thereon. In the sanitary napkin 201 according to the third embodiment, the detailed description of the portions having the same construction as those of the sanitary napkin 1 according to the first embodiment will be omitted by designating them by the common reference numerals.

FIG. 17 shows the vagina-facing reference line X1, perineum-facing reference line X2 and anus-facing reference line X3. FIG. 18 is a sectional view taken along the vagina-facing reference line X1, FIG. 19 is a sectional view taken along the perineum-facing reference line X2, and FIG. 20 is a sectional view taken along the anus-facing reference line X3.

The sanitary napkin 201 has a main body 202 and a projection 203. A cover sheet 223 is disposed on the body surface side of the main body 202 and the projection 203. In the third embodiment, the cover sheet 223 forms not only a part of the main body 202 but also a part of the projection 203.

The cover sheet 223 is a nonwoven fabric that is stretchable in the longitudinal direction, for example, a through-air bonded nonwoven fabric identical to that used for the projection topsheet 31 of the first embodiment. In order to make the cover sheet 223 easily stretchable in the longitudinal direction, the through-air bonded nonwoven fabric or another type of nonwoven fabric such as spunlaced nonwoven fabric may be corrugated to have ridge and grooves extending in parallel to the lateral direction. In the compression line 41, as shown in FIG. 17, the cover sheet 223 is heated and pressed together with the liquid-absorbent layer 22. The area enclosed by the compression line 41 is elongated to extend from in front of the vagina-facing reference line X1 to an area intended to face the coccyx of the wearer's body.

In the overlap of the area enclosed by the compression line 41 and the area behind the vagina-facing reference line X1, as shown in FIGS. 19 and 20, an interior sheet 232 is bonded to the garment surface of the cover sheet 223 through a hot-melt type adhesive that is applied in such an amount as not to interfere with passage of liquid. Between the cover sheet 223 and the interior sheet 232, a plurality of elastic members 233 are interposed while being stretched at least 1.2 times the original length. These elastic members 233 are bonded to both the cover sheet 223 and the interior sheet 232 through the hot-melt type adhesive. For example, the elastic members 233 may be polyurethane elastic filaments having a fineness of about 940 dtex and secured while being stretched 1.4 times the original length.

On or in front of the vagina-facing reference line X1, as shown in FIG. 18, the cover sheet 223 is bonded to the body surface of the liquid-absorbent layer 22 through a hot-melt type adhesive 235 that is applied in such an amount as not to interfere with passage of liquid. Also behind the rear rising reference line X4, the cover sheet 223 is bonded to the body surface of the liquid-absorbent layer 22.

The elastic members 233 exert a longitudinal elastic contractive force on the cover sheet 223 at least between the vagina-facing reference line X1 and the rear rising reference line X4. The rear rising reference line X4 is intended to face the intergluteal cleft behind the anus or the coccyx behind the intergluteal cleft. As a result, when no external force is exerted thereon, the sanitary napkin 201 is longitudinally curved to bring the vagina-facing reference line X1 and the rear rising reference line X4 closer to each other. In the overlap of the area between the vagina-facing reference line X1 and the rear rising reference line X4 and the area enclosed by the compression line 41, therefore, the cover sheet 223, the interior sheet 232 and the elastic members 233 are raised away from the body surface of the liquid-absorbent layer 22. In the third embodiment, the projection 203 is formed of the cover sheet 223, the interior sheet 232 and the elastic members 233.

On the perineum-facing reference line X2, as shown in FIG. 19, a hump 234 bulges from the body surface of the main body 202 to function as a resistive member. The hump 234 may be formed by locally increasing the basis weight of the liquid-absorbent layer 22 or pressing the liquid-absorbent layer 22 in the thickness direction in an area other than the hump 234. In the third embodiment, the liquid-absorbent layer 22 may be a mixture of softwood kraft pulp and superabsorbent polymer. The liquid-absorbent layer 22 may have a largest basis weight (e.g., 900 g/m$^2$) at the hump 234 and a second largest basis weight (e.g., 700 g/m$^2$) between the front end of the hump 234 and the front end portion 41a of the compression line 41. In the other area, the liquid-absorbent layer 22 may have a small basis weight (e.g., 400 g/m$^2$). The liquid-absorbent layer 22 may be heated and pressed in the thickness direction, except the hump 234.

As shown in FIGS. 19 and 21, the body surface of the hump 234 is bonded to the garment surface of the interior sheet 232 through a hot-melt type adhesive 236 that is applied in such an amount as not to interfere with passage of liquid. Within the area between the vagina-facing reference line X1 and the rear rising reference line X4, the liquid-absorbent layer 22 remains unsecured to the interior sheet 232, except the hump 234.

When the sanitary napkin 201 is applied to the wearer's crotch in such a curved state as shown in FIG. 21, the projection 203 is highly resistant to compressive deformation toward the main body 202 at the resistive portion where the hump 234 is provided as a resistive member, as described with reference to FIG. 7. Thus, the resistive portion of the projection 203 can easily be kept in contact with the perineum.

Since the interior sheet 232 is bonded to the hump 234, when a body pressure is exerted on the projection 203 in front of the hump 234, the interior sheet 232 and the cover sheet 223 receive a tensile force due to the body pressure. The cover sheet 223 under tension can be stretched to conform to the vaginal opening. Also behind the hump 234, the interior sheet 232 and the cover sheet 223 receive a tensile force due to the body pressure, and the interior sheet 232 under tension can be stretched to conform to the anus and the intergluteal cleft.

In the sanitary napkin 201, moreover, the area provided with the hump 234 has a higher bending stiffness than the other area, which ensures independent curvature of the sanitary napkin 201 in front of and behind the hump 234 and effectively prevents folding or twisting of the sanitary napkin 201.

When the projection 203 is in contact with the vaginal opening, menstrual blood discharged from the vaginal opening can be collected by hydrophilicity of the cover sheet 223 and the interior sheet 232 of the projection 203. The collected menstrual blood will pass through or flow down the projection 203 and be then absorbed by the liquid-absorbent layer 22, which eases the anxiety of lateral leakage or rearward leakage of menstrual blood. In addition, menstrual blood flowing rearward along the surface of the cover sheet 223 and the liquid-absorbent layer 22 can be stopped and absorbed by the hump 234, which is also effective in preventing rearward leakage of menstrual blood.

Figure 22:
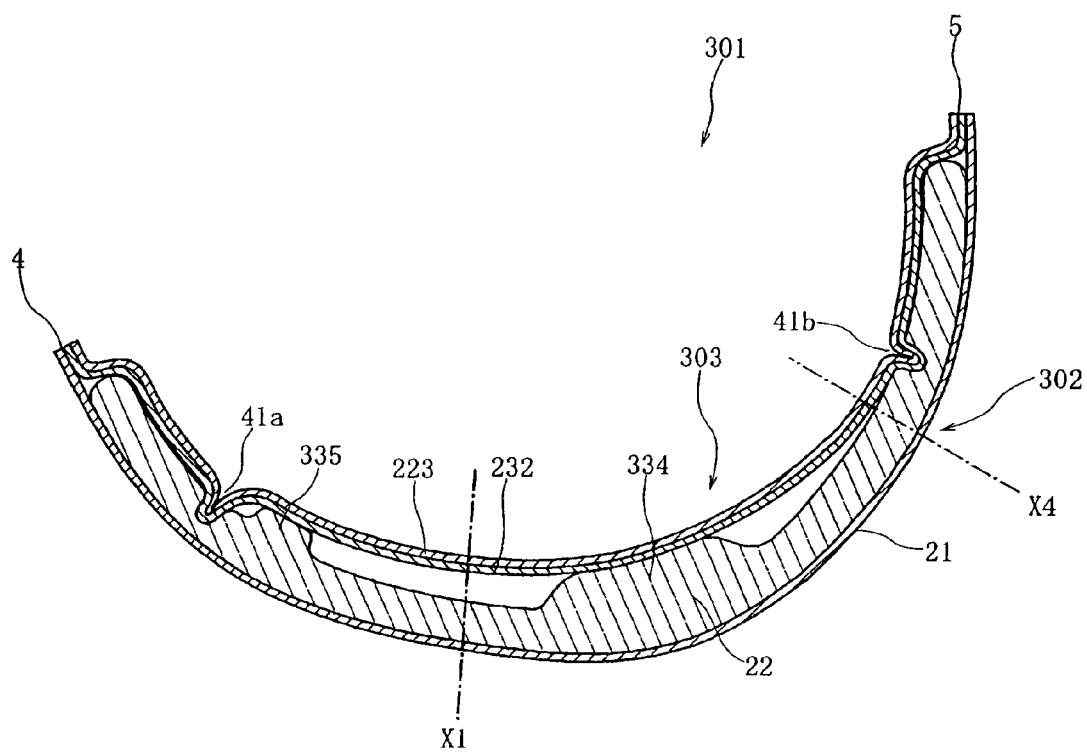
FIG. 22 is a longitudinal sectional view of a sanitary napkin according to a fourth embodiment of the present invention in a state where no external force is exerted thereon.

FIG. 22 is a longitudinal sectional view of a sanitary napkin 301 according to a fourth embodiment of the present invention. The sanitary napkin 301 is a modification of the sanitary napkin 201 shown in FIG. 21.

The sanitary napkin 301 has a main body 302 in which the liquid-absorbent layer 22 is formed not only with a hump 334 that is similar to the hump 234 but also with a front hump 335 immediately behind the front end portion 41a of the compression line 41. A projection 303 is formed of the cover sheet 223, the interior sheet 232 and the elastic members 233. The elastic contractive force exerted by the elastic members 233 acts between the front hump 335 and the rear rising reference line X4. The interior sheet 232 is bonded to both the body surface of the hump 334 and the body surface of the hump 335.

When the sanitary napkin 301 is worn, the hump 334 is intended to face the perineum or the anus while the front hump 335 is intended to face the skin in front of the vaginal opening. Accordingly, the intermediate portion between the hump 334 and the hump 335 is intended to face the vaginal opening. In this intermediate portion, a space is left between the liquid-absorbent layer 22 and the laminate of the cover sheet 223 and the interior sheet 232. When subjected to a body pressure, accordingly, the cover sheet 223 is stretched between the humps 334, 335 to ensure contact with the vaginal opening. Moreover, longitudinal migration of menstrual blood discharged from the vaginal opening and applied to the intermediate portion between the humps 334, 335 can be blocked by the humps 334, 335. This is effective in preventing forward and rearward leakage of menstrual blood.

Figure 23:
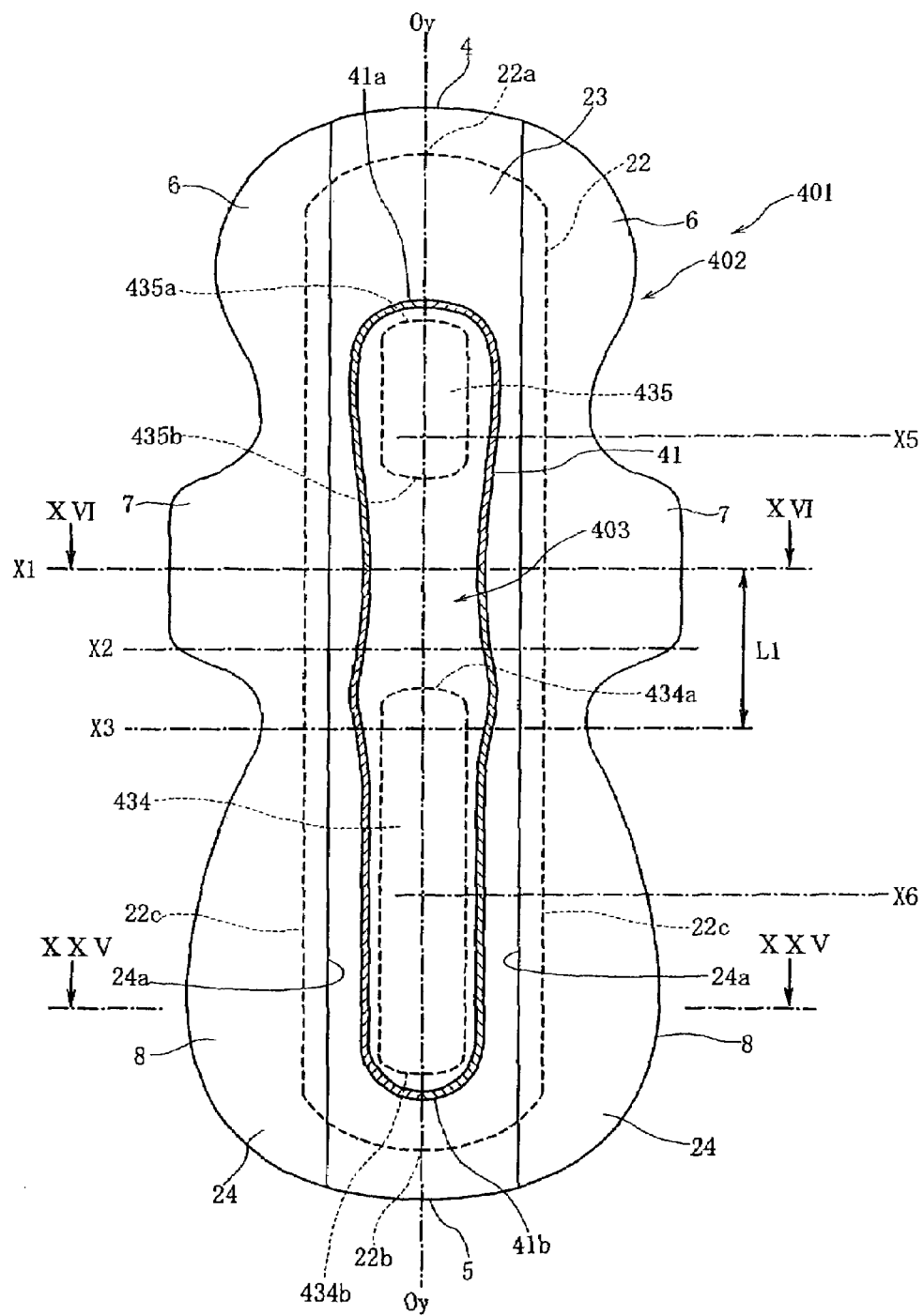
FIG. 23 is a plan view of a sanitary napkin according to a fifth embodiment of the present invention in a flattened state.
Figure 24:
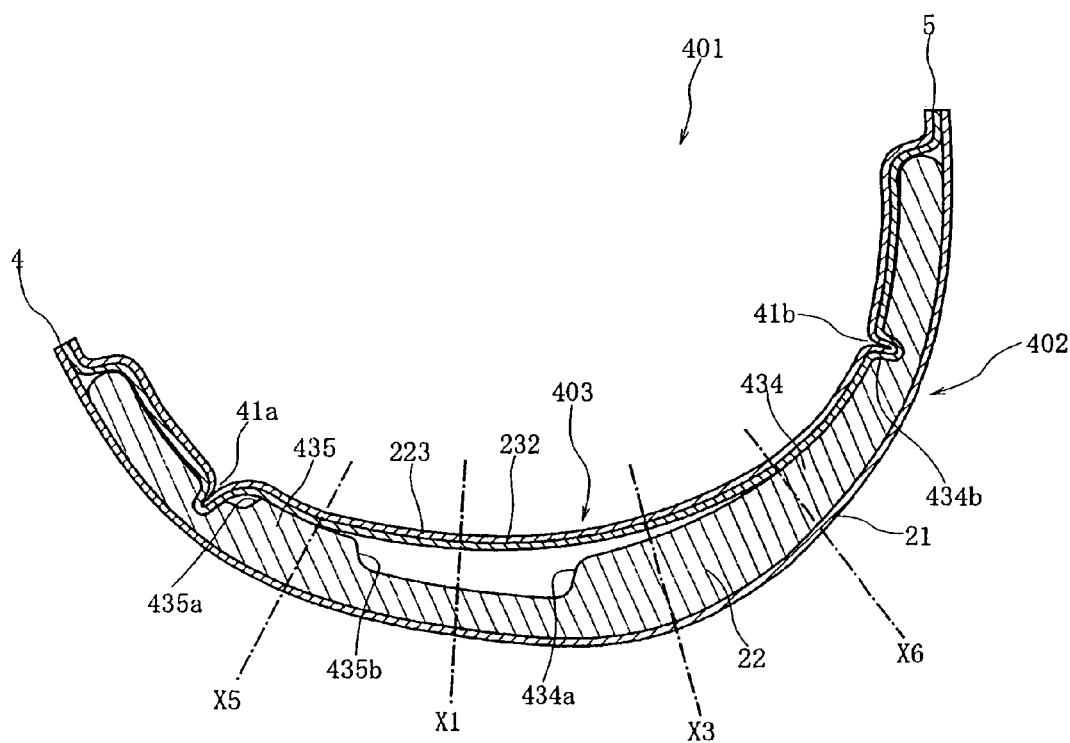
FIG. 24 is a longitudinal sectional view of the sanitary napkin of FIG. 23 in a state where no external force is exerted thereon.
Figure 25:
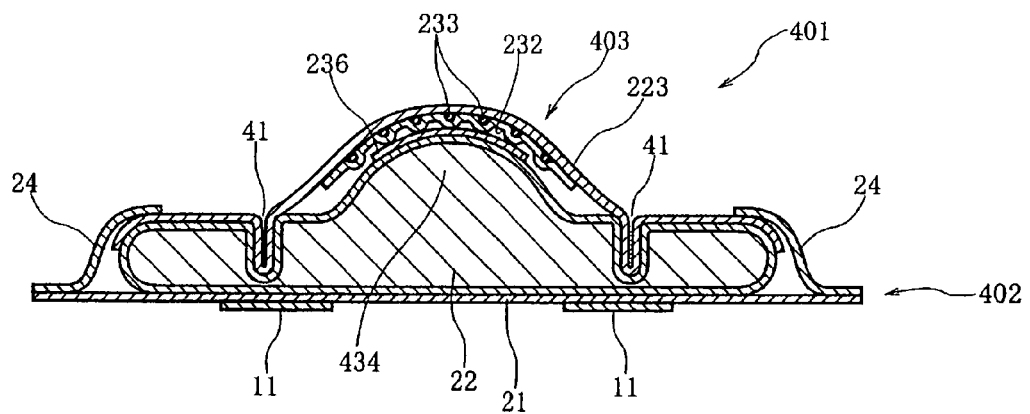
FIG. 25 is a sectional view taken along line XXV-XXV of FIG. 23.
Figure 26:
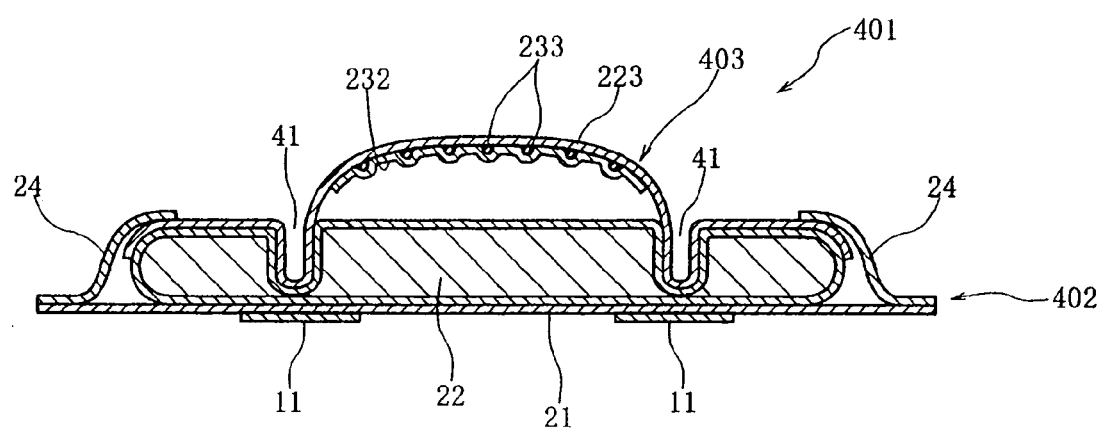
FIG. 26 is a sectional view taken along line XVI-XVI of FIG. 23.

FIG. 23 is a plan view of a sanitary napkin 401 according to a fifth embodiment of the present invention in a flattened state. FIG. 24 is a longitudinal sectional view of the sanitary napkin 401 taken along the longitudinal centerline Oy in a curved state where no external force is exerted thereon. FIG. 25 is a sectional view taken along line XXV-XXV of FIG. 23, and FIG. 26 is a sectional view taken along line XVI-XVI of FIG. 23. The sanitary napkin 401 is a modification of the sanitary napkin 301 shown in FIG. 22.

In the sanitary napkin 401, as shown in FIG. 23, the compression line 41 is formed in the body surface of a main body 402 to enclose a longitudinally elongated area. In the area enclosed by the compression line 41, there is formed a projection 403.

In the area enclosed by the compression line 41, the main body 402 has longitudinally spaced humps 434, 435. The liquid-absorbent layer 22 has a larger basis weight in the rear and front humps 434, 435 than in an intermediate portion between the humps 434, 435. As shown in FIG. 23, the rear hump 434 has a front end 434a that is spaced about 50 mm rearward from the vagina-facing reference line X1 and a rear end 434b that is spaced slightly forward from the rear end portion 41b of the compression line 41. The front hump 435 has a rear end 435b that is spaced about 50 mm forward from the vagina-facing reference line X1 and a front end 435a that is spaced slightly rearward from the front end portion 41a of the compression line 41. The rear hump 434 has a smaller width than the front hump 435. For example, the rear hump 434 has a width of 30 mm and the front hump 435 has a width of 35 mm.

The projection 403 is formed of the cover sheet 223, the interior sheet 232 and the elastic members 233. The longitudinal elastic contractive force exerted by the elastic members 233 acts on the cover sheet 223 between front and rear reference lines X5, X6 shown in FIG. 23. Behind the rear reference line X6, as shown in FIG. 25, the interior sheet 232 and the cover sheet 223 are firmly secured to the body surface of the hump 434 through the hot-melt type adhesive 236 that is applied in such an amount as not to interfere with passage of liquid. Also in front of the front reference line X5, the interior sheet 232 and the cover sheet 223 are firmly secured to the body surface of the hump 435.

Between the front and rear reference lines X5, X6, the interior sheet 232 and the cover sheet 223 remain unsecured to the humps 434, 435. Accordingly, the longitudinal elastic contractive force exerted by the elastic members 233 acts between the front and rear reference lines X5, X6, causing longitudinal curvature of the main body 402 to raise the cover sheet 223 and the interior sheet 232 away from the body surface of the main body 402 between the front and rear reference lines X5, X6.

In the sanitary napkin 402, the cover sheet 223 of the projection 403 comes into contact with the vaginal opening at a midway position between the front end 434a of the hump 434 and the rear end 435b of the hump 435, while the rear hump 434 faces the anus and the intergluteal cleft. When the sanitary napkin 401 is subjected to a body pressure, the humps 434, 435 can be compressed while resisting the deformation to some extent, and the cover sheet 223 under tension can be stretched between the humps 434, 435. This tension ensures contact of the cover sheet 223 with the vaginal opening.

Although the present invention has been illustrated and described with respect to exemplary embodiments thereof, it should be understood by those skilled in the art that the foregoing and various other changes, omission and additions may be made therein and thereto, without departing from the spirit and scope of the present invention.

The stiffening member 34 employed for the sanitary napkin 1 of the first embodiment and the stiffening member 134 employed for the sanitary napkin 101 of the second embodiment may be made of any suitable materials as long as they are elastically deformable in a wet state. For example, they may be made of a resin foam sheet such as polyurethane foam and polyethylene foam or a 20-100 g/m$^2$ through-air bonded nonwoven fabric manufactured from thick synthetic resin fibers having a fineness of 5.5 to 11 dtex.

The cover sheet 123 employed for the sanitary napkin 101 of the second embodiment so as to exert an elastic contractive force may be a spunbonded or point-bonded nonwoven fabric including polyurethane fibers having a fineness of 1.1 to 11 dtex or a liquid-permeable polyurethane resin film with a large number of apertures for passage of liquid. Also in the sanitary napkin 201 of the third embodiment, the sanitary napkin 301 of the fourth embodiment, and the sanitary napkin 401 of the fifth embodiment, the cover sheet 223 may be the above nonwoven fabric or resin film which can exert an elastic contractive force. In this case, the elastic members 233 may be omitted.

Furthermore, the projection-forming member 132 employed for the sanitary napkin 101 of the second embodiment may be a through-air bonded nonwoven fabric or another type of nonwoven fabric manufactured from synthetic resin fibers treated to be hydrophilic.

The present invention should not be understood as limited to the specific embodiments set out above but should be understood to include all possible embodiments which can be embodied within a scope encompassed and equivalent thereof with respect to the feature set out in the appended claims.

What is claimed is:

1. A sanitary napkin comprising:
   a main body having a liquid-absorbent layer for absorbing and retaining liquid; and
   a projection separately provided on a body surface of the main body, the projection having a liquid-permeable projection topsheet and a projection interior sheet,
   wherein the projection comprises
      a stiffening member comprising a folded sheet, the stiffening member being located fully behind-a vagina-facing reference position and in front of or on an anus-facing reference position, the vagina-facing reference position being selected to correspond to the center of a vaginal opening of a wearer of the sanitary napkin, and the anus-facing reference position being selected to face the anus;
      a flexible portion including front and rear flexible portions respectively located in front of and behind the stiffening member, the flexible portion being subjected to a longitudinal elastic contractive force;
      a plurality of longitudinal elastic members for exerting the longitudinal elastic contractive force, spaced apart from each other along the projection interior sheet, wherein the elastic members are held between confronting faces of the projection interior sheet, and
      a hollow space,
   wherein the main body is concavely curved by the longitudinal elastic contractive force,
   wherein the stiffening member comprises a plurality of compression lines each having a first portion that extends perpendicularly from a longitudinal direction of the main body and a second portion that extends upwardly from the main body, and
   wherein the flexible portion is further secured to a convex part of the main body and unsecured to the main body in front of and behind the convex part.

2. The sanitary napkin of claim 1, wherein a bending stiffness in a direction of the curvature is higher in an area provided with the resistive member than in the other area.

3. The sanitary napkin of claim 1, wherein the stiffening member is disposed on rising walls of the projection.

4. The sanitary napkin of claim 1, wherein the stiffening member is a hump bulging from the body surface of the main body.

5. The sanitary napkin of claim 4, wherein the flexible portion is secured to the hump and unsecured to the main body in front of and behind the hump.

6. The sanitary napkin of claim 4, wherein the hump includes a plurality of longitudinally spaced humps.

7. The sanitary napkin of claim 1, wherein the liquid permeable projection topsheet covers the entire body surface area of the projection.

8. The sanitary napkin of claim 1, wherein the stiffening member is a fulcrum; the stiffening member providing increased bending stiffness of the sanitary napkin such that the sanitary napkin can be curved, and the front and rear flexible portions can conform to the contour of the wearer's body.

* * * * *